(12) United States Patent
Huang et al.

(10) Patent No.: US 8,652,539 B1
(45) Date of Patent: Feb. 18, 2014

(54) MITOCHONDRIA REGULATOR COMPOSITION

(71) Applicant: National Taiwan University, Taipei (TW)

(72) Inventors: Ching-Jang Huang, Taipei (TW); Kan Ni Lu, Taipei (TW); Hsin-Sheng Tsay, Taipei (TW); Emily Chin-Fun Chen, Taipei (TW); Chung-Huang Tsai, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/731,631

(22) Filed: Dec. 31, 2012

(30) Foreign Application Priority Data

Aug. 13, 2012 (TW) .............................. 101129306 A

(51) Int. Cl.
*A01N 65/00* (2009.01)
(52) U.S. Cl.
USPC ......................................................... 424/725
(58) Field of Classification Search
None
See application file for complete search history.

(56) References Cited

U.S. PATENT DOCUMENTS 8,362,297 B2 * 1/2013 Scheele ........................ 562/553

* cited by examiner

*Primary Examiner* — Michael Meller
(74) *Attorney, Agent, or Firm* — WPAT, P.C.; Anthony King

(57) ABSTRACT

The present invention provides a mitochondria regulator composition, which comprises a wild bitter gourd extract. The mitochondria regulator composition can regulate the function of mitochondria in a cell, and further regulate the efficiency of adaptive thermogenesis and energy expenditure in a cell.

1 Claim, 5 Drawing Sheets

MITOCHONDRIA REGULATOR COMPOSITION

CROSS-REFERENCE TO RELATED APPLICATIONS

This application claims the priority of Taiwanese Patent Application No. 101129306, filed on Aug. 13, 2012, which is incorporated herewith by reference in its entirety.

BACKGROUND OF THE INVENTION

1. Field of the Invention

The present invention relates to a cell regulator, especially relates to a mitochondria regulator.

2. The Prior Arts

No matter at rest or at work, normal function of human organs and tissues must have adenosine triphosphate (abbreviated as ATP) involved. In cells about 90% of the ATP is generated by mitochondria, and oxygen is consumed when mitochondria produces ATP. It is estimated that 90% of the oxygen in the cell are used by mitochondria. Furthermore, when mitochondria metabolize three major nutrients (fatty acids, carbohydrates, and amino acids) efficiently, oxygen will be consumed no matter energy generated or heat generated. Therefore, mitochondria itself is high oxygen consuming organelle and mitochondria is the site with highest frequency of oxidation and reduction reactions in the cell.

In human cell, skeletal muscle use ATP most frequently. ATP required for muscle fiber contraction is dependent on vigorous oxidative phosphorylation reaction in mitochondria. Therefore, there are more blood vessels around the muscle fibers in order to provide enough oxygen and fuel molecules (i.e., fatty acids, carbohydrates, or amino acids).

In addition, fatty tissues in the body can be classified into two groups, namely white adipose tissue and brown adipose tissue, according to their mitochondria type, distribution site in the body and color. The white adipose tissue has smaller and less amount of mitochondria, and the fatty acids in the tissue serve as energy source during rest state and oxidative exercise. On the other hand, the brown adipose tissues are mainly distributed in the shoulder, neck and arm of hibernating animals, and have abundant of mitochondria. Because mitochondria contain many cell pigments, these pigments makes brown adipose tissue exhibits brown color.

Although oxidative metabolism in cellular mitochondria produces ATP, mitochondria in the brown adipose tissue are not designed to produce ATP as a mode of energy output. Especially, there are many thermogenin distributed on the inner membrane of mitochondria in the brown adipose tissue. The thermogenin is a protein that consumes all energy generated by oxidation of fuel molecules, thus no ATP can be generated. Instead, heat is produced and the energy is dissipated. Because the mitochondria in the brown adipose tissue are large and abundant, more heat is produced.

Therefore, brown adipose tissues rely on the unique heat generation system of mitochondria to oxidize fatty acids at low temperature or during ingestion. Without exercise, hibernating animals and newborn babies can also generate heat to adapt cold environment. Because the central temperature regulation system in the newborn babies is not mature, the heat production mode of brown adipose tissue is especially important to protect the newborn babies from tremble reaction. The thermogenin in the mitochondria of brown adipose tissue is an important factor to keep thermostasis.

The above thermogenin apply uncoupling reaction to reduce ATP generation in mitochondria, increase basic metabolism consumption and dissipate energy in heat form. Uncoupling protein (abbreviated as UCP) plays an important role as regulator in mitochondrial's uncoupling reaction. UCPs are proteins located in the inner membrane of mitochondria and there are three main expression forms, including UCP1, UCP2, and UCP3. UCP2 and UCP3 are mainly responsible for regulation of reactive oxygen species (ROS) synthesis. The expression levels of UCP2 and UCP3 are far less than that of UCP1 in mammals. UCP1, also called as "thermogenin", is mainly expressed in brown adipose tissue and is mainly responsible for adaptive regulation of heat generation and heat consumption.

Peroxisome proliferator-activated receptor γ coactivator-1 (PGC1α), tfam (mitochondrial transcription factor A) and NrF1 (nuclear respiratory factor 1) are important transcription regulation factors in mitochondria biosynthesis, wherein PGC1α is a coactivator of PPARγ that mainly distributed in high oxygen consumption tissue, such as heart tissues or brown adipose tissues. PGC1α can regulate mitochondria biosynthesis and energy metabolism. Furthermore, tfam can bind to mitochondria DNA to regulate mitochondria transcription and replication, and NrF1 is also involved in regulation of mitochondria gene transcription. Prior studies have shown that increase of PGC1α concentration in the muscle can stimulate expression of abovementioned NrF and tfam of mitochondria genes, decrease possibility of obesity owing to aging, and decrease possibility of diabetes, and prolong life.

The material, bitter gourd, is a common traditional Chinese medicine. However, to the best of our knowledge, the bitter gourd has never been reported in regulation the mitochondria. The mitochondria regulator can modulate mitochondrial related proteins and genes effectively to enhance heat and energy generation efficiency. The mitochondria regulator composition of the present invention can be used as a healthy food composition or pharmaceutical composition for treatment of disease due to deficiency of thermogenin or mitochondria, mitochondrial dysfunction, mitochondria malfunction, or mitochondria dysregulation.

SUMMARY OF THE INVENTION

However, the prior studies of bitter gourd mainly focused on reduction of blood sugar, anti-oxidation activity, and regulation of immune reaction. The present invention discloses that the bitter gourd has significant ability to regulate biosynthesis of intracellular mitochondria and to improve production of energy and heat.

Therefore, the present invention provides a mitochondria regulator composition for regulating a mitochondria in a cell, which consisting essentially of a bitter gourd extract. The cells can be a white adipose tissue cell, a brown adipose tissue cell, or a muscle cell. One embodiment of the present invention, the bitter gourd extract of the present invention is used at least 5% of total diet.

In one example of the present invention, the mitochondria regulator composition can enhance the expression of UCP1 gene (SEQ ID NO:9), PGC1α gene (SEQ ID NO:4), or NrF1 gene (SEQ ID NO:12) in the white adipose tissue cell.

In another example of the present invention, the mitochondria regulator composition can enhance the expression of PGC1α (SEQ ID NO:4) or NrF1 (SEQ ID NO:12) in the brown adipose tissue cell.

In another example of the present invention, the mitochondria regulator composition can enhance the expression of PGC1α gene (SEQ ID NO:4) or tfam gene (SEQ ID NO:13) in the muscle cell.

The present invention also provides a method of regulating a mitochondria in a cell, comprising administering to a subject an effective amount of a bitter gourd extract, wherein the cell can be a white adipose tissue cell, a brown adipose tissue or a muscle cell. In one example of the present invention, the bitter gourd extract is a freeze-dry powder of whole bitter gourd fruit.

Wherein, the bitter gourd extract can enhance the expression of UCP1 (SEQ ID NO:9), PGC1α (SEQ ID NO:4), or NrF1 (SEQ ID NO:12) to regulate mitochondria activity in the white adipose tissue; can enhance the expression of can enhance PGC1α (SEQ ID NO:4), or NrF1 (SEQ ID NO:12) to regulate mitochondria activity in the brown adipose tissue; and can enhance the expression of PGC1α (SEQ ID NO:4) or tfam (SEQ ID NO:13) to regulate mitochondria activity in the muscle cell.

Using the bitter gourd extract of the present invention, the function of intracellular mitochondria can be regulated by enhancement of mitochondria biosynthesis and generation of heat, which further leading to regulation of heat generation and energy consumption efficiency.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

DETAILED DESCRIPTION OF THE PREFERRED EMBODIMENT

Figures 1A, 1B:
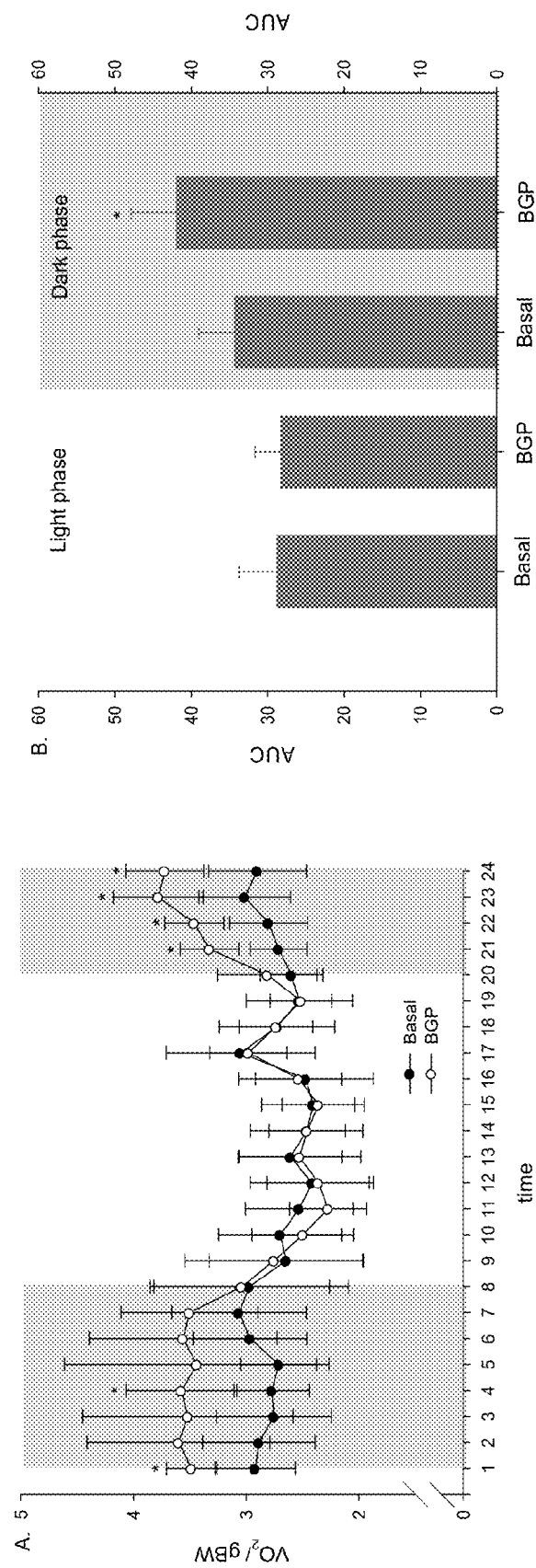
FIG. 1A shows the oxygen consumption per gram body weight ($VO_2$/gBW) of mice in 24 hours.
FIG. 1B shows a comparison of the area under curve of FIG. 1A.

The present invention uses mice for study. Mice are divided into two groups, the control group and the experimental group. The diet of the experimental group contains 5% of wild bitter gourd powder, therefore, this group is also named as BGP group. The diet of the control group is a modification of AIN-93G basic diet, therefore, this group is also called Basal group.

Because increase of mitochondria biosynthesis and increase of heat and energy generation efficiency require consumption of oxygen, mice fed with experimental diet were monitored their oxygen consumption, $CO_2$ production, and respiratory quotient at week 5. The oxygen consumption, $CO_2$ production, and respiratory quotient of experimental group were compared with control group to examine if elevation trend was observed. If yes, further analysis of mRNA was conducted to determine if increase of mitochondria biosynthesis and increase of heat and energy generation efficiency contributed to elevation of oxygen consumption, $CO_2$ production, and respiratory quotient. mRNA analysis was conducted by sampling of white adipose tissue, gastrocnemius, and brown adipose tissue of experimental group mice at 22 week for mRNA and protein analysis. If the BGP group mice fed with diet incorporating 5% wild bitter gourd showed significant elevation of fatty acid oxidation, adapted heat generation, and gene or protein related to mitochondria biosynthesis, the results provided evidences that wild bitter gourd can enhance mitochondria biosynthesis and increase efficiency of heat and energy generation. The above described methods are further explained in the following examples.

Data of the present invention are presented as means±SD. Differences between the two groups of mice were analyzed by Student's t test. Data was transformed into log or root square before statistic analysis if they are not normally distributed. P value <0.05 was considered significant.

Definition

The term "regulator" of the present invention is intended to mean capability to enhance or reduce an activity. Therefore, the mitochondria regulator composition of the present invention for use in regulation of mitochondria as described in the specification is intended to mean the use of the mitochondria regulator composition in direct contact with the mitochondria. In further examples, the mitochondria regulator composition of the present invention can be administered an effective amount to an individual when mitochondria require regulation to enhance or increase mitochondria activity.

Example 1

Diet Formulation of Bitter Gourd and Animal Study

Fresh wild bitter gourd (Cultivar Hualien No. 4) fruits were provided by Hualien District Agricultural Research and Extension Station of Taiwan. This cultivar was specifically bred based on a high PPAR activating activity. Whole fruits (included seeds) were washed, sliced, frozen and lyophilized. They were then grounded to produce the bitter gourd powder (BGP) sample and stored at −20° C. for making the BGP test diet.

Twelve eight-week old male C57BL/6J mice for animal studies were purchased from the National Laboratory Animal Center (Taipei, Taiwan). Mice were acclimatized for 4 weeks and fed a non-purified diet (Rodent Chow, PMI Nutrition International, Brentwood, Mo. USA) before the experiment. After acclimation, mice were randomly assigned into two groups. The control group (n=6) was fed AIN-93 modified basal diet wherein carbohydrate sources were provided by 50% sucrose (abbreviated as basal group), while the experimental group (n=6) was fed AIN-93 modified basal diet by incorporating 5% (w/w) of a freeze dried powder of bitter gourd (abbreviated as BGP group). Before the experiment began, the experimental mice were acclimated for bitter taste for one week. All experimental mice were housed individually in stainless steel wire cages in an animal room with a 12 hour light and 12 hour dark cycle and constant temperature (22±2° C.). Throughout the acclimation and experimental period, mice had free access to water and diet. Diet was changed twice a week, and each mice body weight was recorded every week.

The diet formulations described above are shown in Table 1 below. The basal diet was a modification of AIN-93G diet, wherein the original carbohydrate source (62.95% of corn starch) was replaced by mixture of corn starch (Samayang genex, Korea) and sucrose in 12.95:50 ratio. The rest ingredients include casein (ICN, USA), cystine (Wako, Japan), cellulose (JRS, Germany), AIN-93G Vitamin Mix (ICN, USA), AIN-93 Mineral Mix (ICN, USA) and choline (Sigma, USA). To prepare diet, powder materials were mixed well. Then soybean oil (Taiwan Sugar) was added and mixed again. After sieving twice, diet was packaged in double layer sealing bag and stored at −20° C. until use. The BGP diet was formulated by incorporating 5% (w/w) of BGP into the basal diet by slightly adjusting the composition of casein, corn starch, soybean oil and cellulose based on the proximate composition of BGP, i.e., crude protein 4.5%, carbohydrate 54.6%, cellulose 38.2% and crude fat 2.7%.

TABLE 1

Diet Formulation of Basal Group and BGP Group containing Freeze Dried Powder of Hualien No. 4 Bitter Gourd

| Composition % | Basal Group | BGP Group |
|---|---|---|
| Casein | 20 | 19.775 |
| L-Cystine | 0.3 | 0.3 |
| Corn Starch | 12.95 | 10.22 |
| Sucrose | 50 | 50 |
| Cellulose | 5 | 3.09 |
| Soybean Oil | 7 | 6.865 |
| AIN-93G Vitamin Mix | 1 | 1 |
| AIN-93G Mineral Mix | 3.5 | 3.5 |
| Choline | 0.25 | 0.25 |
| Freeze Dried Powder of Hualien No. 4 Bitter Gourd | — | 5 |
| Oligosaccharide | — | — |
| kcal/g | 3.948 | 3.948 |
| fiber/g | 0.05 | 0.05 |
| Energy of carbohydrate/total energy (%) | 63.78 | 63.78 |
| Energy of protein/total energy(%) | 20.26 | 20.26 |
| Lipid energy/total energy(%) | 15.96 | 15.96 |

1. Diet of AIN-93 Vitamin Mix and AIN-93Mineral Mix are prepared according to formulation described in J. Nutt 123: 1939-1951 (1993) (Reeves et al., 1993).
2. Diet of BGP group was prepared incorporating bitter gourd powder into basal AIN-93 basal diet by slightly adjusting the compositions.

Example 2

Oxygen Consumption, Carbon Dioxide Production, and Respiratory Quotient Measurement (Metabolic Chamber Study)

The mice of the example 1 were fed with experimental diet for 5 weeks. The mice were then acclimatized in Oxymax System metabolic chambers (AccuScan Instruments, Inc. Columbus, Ohio USA) for 6 days with free access to the respective diet and water in an animal room kept on a 12 hour light and 12 hour dark cycle (light phase 8:00-20:00; dark phase 20:00-8:00) until steady. After acclimatization, data of the $O_2$ consumption and $CO_2$ production of the mice were automatically monitored and recorded for 24 hours on day 7 and the results were expressed as per gram body weight. The respiratory quotients (RQ) were also calculated as $VCO_2/VO_2$.

Figures 2A, 2B:
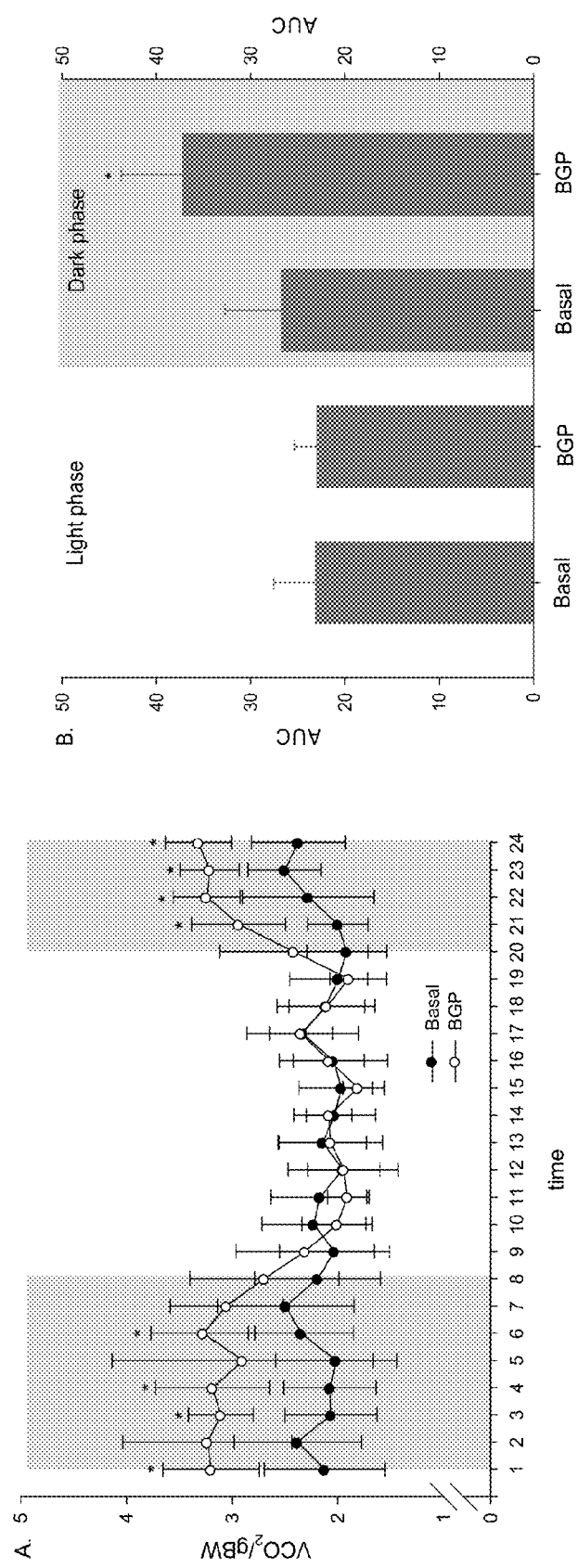
FIG. 2A shows $CO_2$ production per gram body weight ($VCO_2$/gBW) of mice in 24 hours.
FIG. 2B shows a comparison of the area under curve of FIG. 2A.
Figures 3A, 3B:
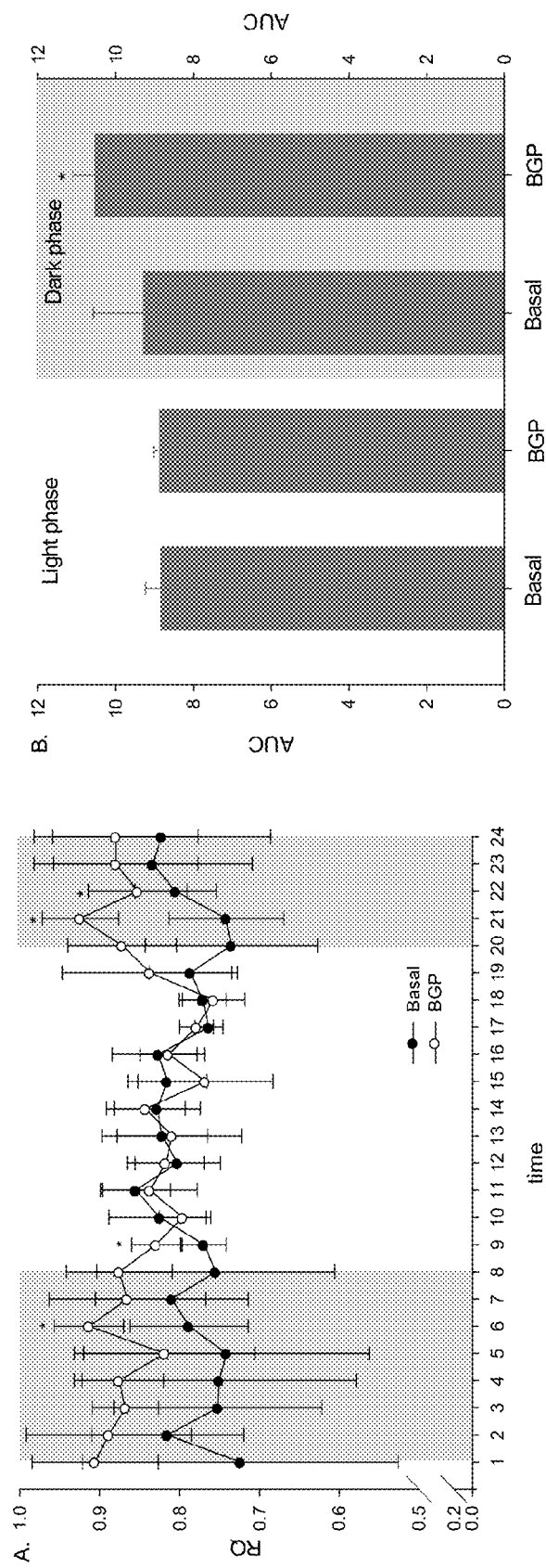
FIG. 3A shows RQ value of mice in 24 hours.
FIG. 3B shows a comparison of the area under curve of FIG. 3A.

The results showed that the experimental group (the BGP group) at different time point of dark phase (20:00-8:00) showed significant increase of oxygen consumption (FIG. 1A) and $CO_2$ production (FIG. 2A, $p<0.05$) per gram body weight. Further calculation of area under curve (abbreviated as AUC) of FIG. 1 and FIG. 2A indicated that the BGP group showed significant increase of oxygen consumption (FIG. 1B) and $CO_2$ production (FIG. 2B, $p<0.05$) in the dark phase as compared to basal group. The $VCO_2$ was further divided by $VO_2$. The obtained results, respiratory quotient (abbreviated as RQ values), were shown in FIGS. 3A and 3B. The RQ values of the BGP group were 0.8-0.9, whereas the RQ values of the basal group were 0.7-0.8. Compared to the basal group, mice in the BGP group had significantly higher $VO_2$ and $VCO_2$ at quite a few time points in the dark phase ($p<0.05$). However, there is no significant difference ($p>0.05$) between the BGP group and the basal group in oxygen consumption, $CO_2$ production, and RQ value when these groups were in the light phase (8:00-20:00).

Therefore, oxygen consumption, $CO_2$ production, and RQ value of the BGP group through the dark phase was significantly higher than that of the basal group, indicating that respiratory activity of the BGP group mice was higher in the dark phase and energy and heat generation efficiency of mitochondria in the BGP group mice has been enhanced. This assumption requires further gene expression analysis to provide objective evidences.

Example 3

Gene Expression Analysis

At the end of 22 week of feeding, mice were feed-deprived at 3 AM in the morning for 16 hours, weigh of body weight and then sacrificed by $CO_2$ asphyxiation. Excise and collect about 0.1 gram of epididymal white adipose tissue (abbreviated as EWAT), gastrocnemius muscle white adipose tissue and intra scapular brown adipose tissue in sterile 1.5 mL centrifuge tube or foil, then weighed and immediately frozen in liquid nitrogen, and then stored at −80° C. until gene expression analysis.

The mRNA expression of the following genes in epididymal white adipose tissue, brown adipose tissue (abbreviated as BAT) or muscle cells were analyzed, including PPARα (SEQ ID NO:1), PPARγ (SEQ ID NO:2), PPARδ (SEQ ID NO:3), and PGC1α (SEQ ID NO:4) genes; fatty acid oxidation related genes: CPT1a (SEQ ID NO:5), CPT1b (SEQ ID NO:6), ACD1 (SEQ ID NO:7), and ACS1 (SEQ ID NO:8); adaptive heat generation related gene: uncoupling protein 1 (UCP1 (SEQ ID NO:9)); cholesterol metabolism related gene and glycolysis related genes: SREBP1 (SEQ ID NO:10) and GK (SEQ ID NO:11); and mitochondria biosynthesis genes NrF1 (SEQ ID NO:12) and tfam (SEQ ID NO:13), wherein PCR primer and probes were purchased from Applied Biosystems.

RNA was isolated using TRIZOL reagent (Invitrogen) according to the instruction. Total RNA (2 μg) was reversed transcribed into cDNA in mixed solution containing 10×Rnt buffer, 100 mM dNTP mix buffer, 10×RT random primer, and MutiScribe™ RTase. Total volume of the polymerase chain reaction (PCR) mixture was 25 μL, containing 10 μL cDNA, 12.5 μL TaqMan® Gene Expression Master Mix, 1.25 μL probe/primer reagent mixture and water. PCR and fluorescence analysis was performed using ABI PRISM7000 Gene Sequence Detection System. Amplification conditions 150 were: 2 min at 50° C., 10 min at 95° C. then 40 cycles of 15 s at 95° C. and 1 min at 60° C.

Figures 4A, 4B:
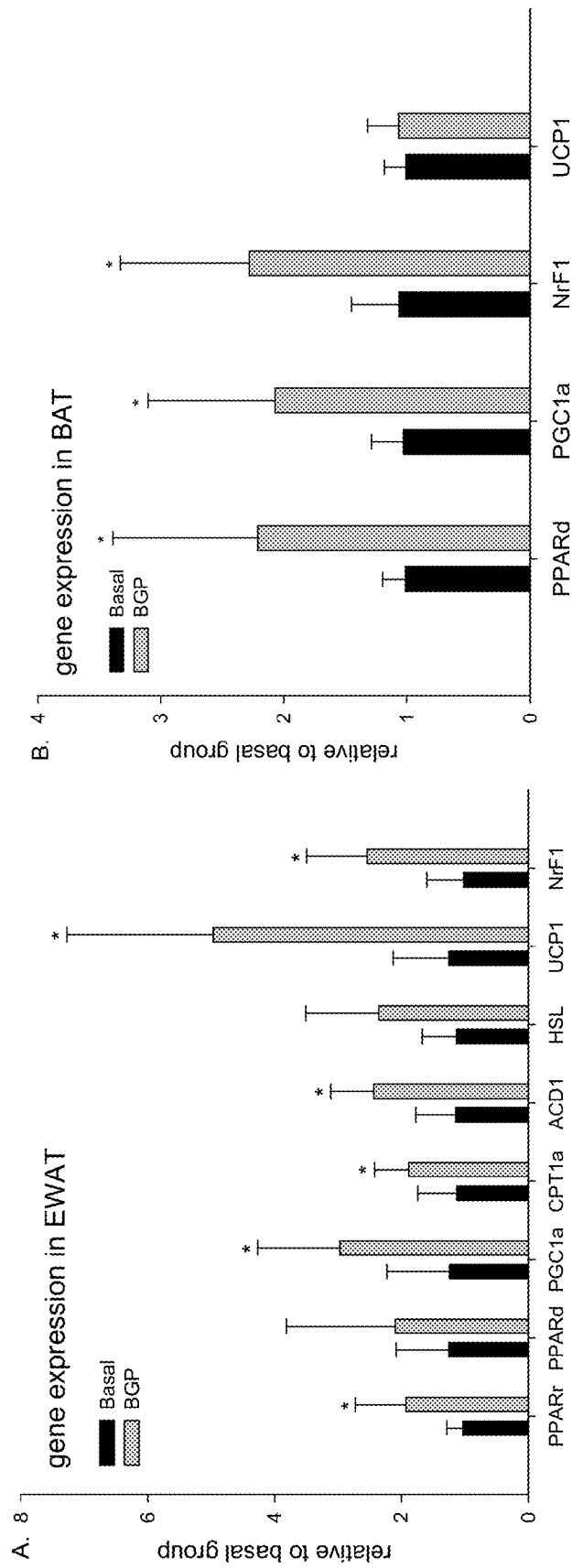
FIG. 4A shows gene expression in epididymal white adipose tissue (EWAT).
FIG. 4B shows gene expression in brown adipose tissue (BAT).
Figure 4C:
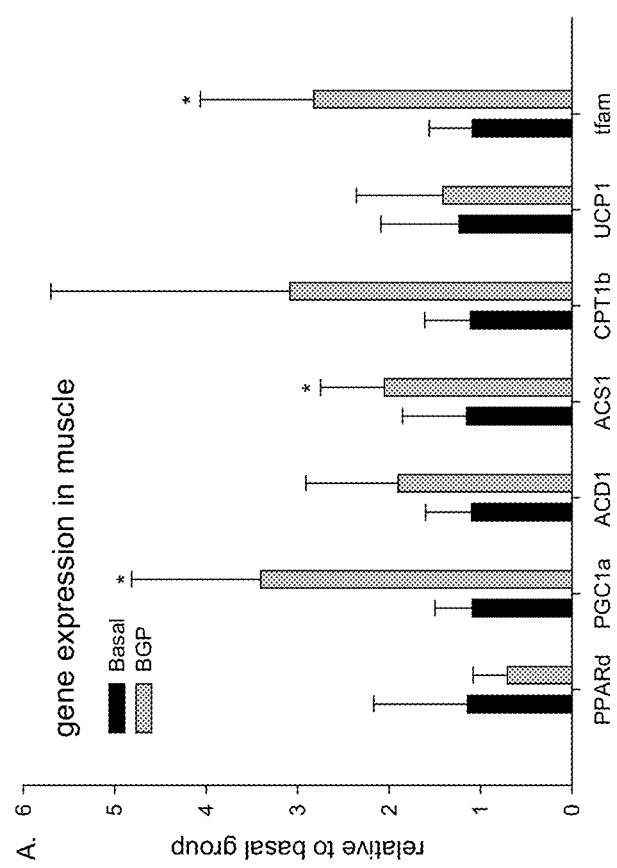
FIG. 4C shows gene expression in the muscle tissue.

Referring to FIG. 4A, in the epididymal white adipose tissue, the BGP group showed significant increase ($p<0.05$) in expression of PPARγ (SEQ ID NO:2), PGC1α (SEQ ID NO:4), fatty acid oxidation gene (CPT1a (SEQ ID NO:5), ACD1 (SEQ ID NO:7)), and uncoupling protein gene 1 UCP1 (SEQ ID NO:9), and Mitochondria biosynthesis gene (NrF1 (SEQ ID NO:12)). Referring to FIG. 4B, in the brown adipose tissue the BGP group showed significant increase ($p<0.05$) of expression in PPARδ (SEQ ID NO: 3), PGC1α (SEQ ID NO:4) and NrF1 (SEQ ID NO:12) genes. Referring to FIG. 4C, in the gastrocnemius muscle the BGP group also showed significant increase of expression ($p<0.05$) of PGC1α (SEQ ID NO: 4), ACS1 (SEQ ID NO:8) and tfam (SEQ ID NO:13) genes.

In summary of the examples above, the results demonstrate that male C57BL/6J mice fed with experimental diet for 22 weeks (the BGP group) show significant increase of oxygen consumption, $CO_2$ production and AUCs. In the aspect of RQ value, the value of the BGP group is close to 1.0, compared to 0.7 of the Basal group. RQ value is the $CO_2$ produced (mole)/ $O_2$ consumed (mole) when carbohydrates or fatty acids are metabolized. The RQ value of glucose oxidation is about 1 and RQ value of fatty acid is around 0.7. Therefore, the BGP group shows significant increase of carbohydrate oxidation when in the dieting phase (dark phase).

Experiments are designed to determine gene expression in gastrocnemius muscle, brown adipose tissue and epidiymal white adipose tissue. The results indicate that BGP group shows significant increase expression of PGC1α (SEQ ID NO: 4), fatty acid metabolism related gene CPT1a (SEQ ID NO: 5) and ACD1 (SEQ ID NO:7), mitochondria biosynthesis gene NrF1 (SEQ ID NO:12) and UCP1 (SEQ ID NO:9) in epididymal white adipose tissue. On the other hand, BGP shows significant increase of expression of PGC1α in gastrocnemius muscle and brown adipose tissue as compared to the control group.

Because PGC1α (SEQ ID NO:4) can regulate heat generation in brown adipose tissue, mice lack of PGC1α (SEQ ID NO:4) expression will die when exposed at low temperature environment due to low body temperature. On the other hand, increase of PGC1α (SEQ ID NO:4) expression in white adipose tissue can enhance activity of mitochondria and increase expression of UCP1 (SEQ ID NO:9). Therefore, the results demonstrate that BGP group mice have enhanced PGC1α (SEQ ID NO:4) gene expression in muscle cell, enhanced PGC1α (SEQ ID NO:4), NrF1 (SEQ ID NO:12) or tfam (SEQ ID NO:13) gene expression in brown adipose tissue cell, and increased PGC1α (SEQ ID NO:4), NrF1 (SEQ ID NO:12) or tfam (SEQ ID NO:13) in white adipose tissue cell, such that mitochondria biosynthesis in the above tissues also increased. Because of this, the test results of the present invention BGP group mice show higher oxygen consumption in the ingestion phase (dark cycle), $CO_2$ production, and energy expenditure, i.e., an increase in RQ value.

Therefore, the mitochondria regulator composition of the present invention can be used as a regulator of mitochondria biosynthesis, or used as an alternative or supplement for control of heat and energy generation. For example, the mitochondria regulator composition of the present invention can be administered an effective amount in treatment of symptoms caused by thermogenin deficiency, the number of mitochondria deficiency, mitochondrial dysfunction, mitochondria malfunction or mitochondria dysregulation; and the mitochondria regulator composition further comprises a pharmaceutical acceptable carrier. In addition, the mitochondria regulator composition of the present invention can be used as a food composition for improvement symptoms of thermogenin deficiency, the number of mitochondria deficiency, mitochondrial dysfunction, mitochondria malfunction or mitochondria dysregulation. The food composition can further contain an additive, wherein the additive can be but not limited to a healthy ingredient, a food ingredient or the combination thereof. The above healthy ingredient can be citric acid, taurine, vitamins, pantothenate, niacin or any other ingredients that may benefit health. The food may be selected from, but not limited to, vegetables, fruits or meats.

What is claimed is:

1. A composition for the regulation of mitochondria biosynthesis consisting essentially of therapeutically effective amounts of whole bitter gourd fruit extract, corn starch and cellulose.

* * * * *

SEQUENCE LISTING

```
<160> NUMBER OF SEQ ID NOS: 13

<210> SEQ ID NO 1
<211> LENGTH: 7216
<212> TYPE: DNA
<213> ORGANISM: Artificial sequence
<220> FEATURE:
<223> OTHER INFORMATION: PPAR alpha

<400> SEQUENCE: 1
ggaggcagcc gcttacgccc ctcctggcgc ctcctcctgg gcgcgcttgg ccctgcggac      60
ccgcaggcgg agtgcagcct cagccaagtt gaagttcaag gccctgcctt ccctgtgaac     120
tgacgtttgt ggctggtcaa gttcgggaac aagacgttgt catcacagct tagcgctctg     180
tggcctgcct ggccacatcc atccaacatg gtggacacag agagccccat ctgtcctctc     240
tccccactgg aggcagatga cctggaaagt cccttatctg aagaattctt acaagaaatg     300
ggaaacattc aagagatttc tcagtccatc ggtgaggaga gctctggaag cttggttttt     360
gcagactacc agtacttagg aagctgtccg ggctccgagg gctctgtcat cacagacacc     420
ctctctccag cttccagccc ttcctcagtc agctgccccg tgatccccgc cagcacggac     480
gagtcccccg gcagtgccct gaacatcgag tgtcgaatat gtggggacaa ggcctcaggg     540
taccactacg gagttcacgc atgtgaaggc tgtaagggct tctttcggcg aactattcgg     600
ctgaagctgg tgtacgacaa gtgtgatcgg agctgcaaga ttcagaagaa gaaccggaac     660
aaatgccagt actgccgttt tcacaagtgc ctgtctgtcg ggatgtcaca caatgcaatt     720
cgctttggaa gaatgccaag atctgaaaaa gcaaaactga agcagaaat tcttacctgt     780
```

```
gaacacgacc tgaaagattc ggaaactgca gacctcaaat ctctgggcaa gagaatccac    840
gaagcctacc tgaagaactt caacatgaac aaggtcaagg cccgggtcat actcgcggga    900
aagaccagca caacccgcc ttttgtcata catgacatgg agaccttgtg tatggccgag    960
aagacgcttg tggccaagat ggtggccaac ggcgtcgaag acaaagaggc agaggtccga    1020
ttcttccact gctgccagtg catgtccgtg agaccgtca cggagctcac agaatttgcc    1080
aaggctatcc caggctttgc aaacttggac ttgaacgacc aagtcacctt gctaaagtac    1140
ggtgtgtatg aagccatctt cacgatgctg tcctccttga tgaacaaaga cgggatgctg    1200
atcgcgtacg gcaatggctt tatcacacgc gagttcctta agaacctgag gaagccgttc    1260
tgtgacatca tggaacccaa gtttgacttc gctatgaagt tcaatgcctt agaactggat    1320
gacagtgaca tttccctgtt tgtggctgct ataatttgct gtggagatcg gcctggcctt    1380
ctaaacatag gctacattga agttgcag gaggggattg tgcacgtgct taagctccac    1440
ctgcagagca accatccaga tgacaccttc ctcttcccaa agctccttca aaaaatggtg    1500
gaccttcggc agctggtcac ggagcatgcg cagctcgtac aggtcatcaa gaagaccgag    1560
tccgacgcag cgctgcaccc actgttgcaa gagatctaca gagacatgta ctgatctttc    1620
ctgagatggc aggccgttgc cactgttcag ggacctccga ggcctgcggc cccatacagg    1680
agagcaggga tttgcacaga gggcctccct cctacgcttg gggatgaaga gggctgagcg    1740
taggtaatgc gggctctccc cacatccttt ctgaatgggc acttctaaga ctacctgcta    1800
ccgaaatggg ggtgatcgga ggctaatagg attcagacag tgacagacaa cggcagtccc    1860
cagtctggtc ttaaccggcc caatgttaat caatgcacag cactctacgt tgcgtttata    1920
attcgccatt aattaacggg taacctcaaa gtctgagcgg tctgttccct tcctgccacc    1980
cttctggcta tgtgcactct cttaaatccc tgaaaactaa tctgcacttt ttaacctttg    2040
aaaacctaca agtcaaggtg tggcccaagg ttagccattt aaatgtggca aaaaaaaaa    2100 aaaatgttta ttgggaagac ttcacttgag tttcctggct ctaagaaaga gagctggctt    2160
ctgagaacat tcgagaatag tttgataagc tatcccatca ctctctctgt gggctcactg    2220
ttctggaggg tgtaactgac tcatgagggt ggggatgggg ggtggggagc attttcagat    2280
ttgtgtagaa gattcccaga aagttacatc ttcaagaagc cctcagaagg cctccgctag    2340
tgtccgatag acaaagacag gatgagccct gagcaggtag ttctgcacct ctgttcatgt    2400
cagaccctca gcgtgtgggc atggcagcaa tatcagaggt agattcacaa aagatttgta    2460
aatgctcctc taggcccctc ctttggcagc tcctttgata tgatacttta ctgctttgta    2520
aaaaacaaaa acaaaaacaa acaaacaaaa aaaaacctct cttggtgatg agatgcgctc    2580
tctctatctc tctggagtag agaaggcaaa agtgacttcg ctatccaggc agaagggagc    2640
tggtcgcctt ggagaacaag agacgagggt gtgatttcat ccagcttctg tttgtaccca    2700
gcagaagagc tcacaacact tggttggtct gtggttattg ttgttgttgt tgttattgtt    2760
gttgtttcaa agaattaggt ggtaaagtcc cttttcctca gtccctgggg aaagcagtgc    2820
tggctacctt caaaagaaac agttgcacaa aggagtctca gacctcatgg actcccggca    2880 cccacccctcc aagggggtgg ctacatattt cagagcaggt tgcaccttct acgctcccga    2940
cccatcttta gaaaactggc catcttctga cgtcatcatc atttgtgatt aaagaatgat    3000
ccagatggac actgccaagg agtcgaggat gtagcccagt ggatggaggg gcttggttcc    3060
tggtgccgat ttatgacat ggtggtagat gcctgcaacc ccagcagaag tcagaggtcg    3120
ccttcagata cataattaag tgggatgcta gtctgtgccg tgtgagaccc tgtttaaaag    3180
```

```
agaaaaagat tgctgctgac gaaatgttca aggtcagcat tatgaaaaca ctaataagaa    3240
taataataag ggaaaattag cattgggaca tactttaaga tttgcaccct tactgacctt    3300
ccccactccc tcctgctctt ccttctcccc tcctccctgt cttctgtcct tcctcaaacc    3360
cacttgcccc ctttgtcttc cctccttgct gccaatcaaa ggctctgttg dacagcagtt    3420
gctgcaggca gtctgccaag gctcttagga atcagagggc agagcaagtc atcttcatgt    3480
atgatcctgg tgagggttga gctcagtcag gaaggagcca gcctttgtgt cacatggcac    3540
agccagtcct cagtgcttcc agagggagag ctggtcctat gtttggaagg tccctagga    3600 ggacaggatc ctgttctggt gaatcttaga caaatgccac tcgtaggtga ccttggaaag    3660
ggagttttga gtcatgggct ttcgggatag ttgagcattc tgtttgaact cgcctaaaac    3720
ttatgaagag tagtcccttg ctgtgtgcct tcagcatgga ccaactgact gacaagttcc    3780
gtgtcagtct gcatctgagc tgatgctcag tcgagttcat gcaagtttcg ttctcctgga    3840
gcctcgtggg actgccagta agctatccct agagaagcca ggaggaacca cagtggcctt    3900
ggcttcaaag tcagtgactc tgtgtacatg taccttcctt tatgggaagg atattcacaa    3960
tgtggccaca tggtgctagg acctttcagg tcacctagtc agatttctca aggccttagt    4020
aacccaagac atgccaggtt aaatactgtg acacacttag gaactgagaa agctggcagc    4080
tatgctctgc aaggtgtgtc agtggcatca gccaacagcc caatcagaga tgccaccttg    4140
gctcctggag ctctagagca gggttgcaaa gccacttccc agcactgatg gcaaagtctt    4200
agtgccagac tccttggaga ccgatgggga ccaggcagcc ttggtgtccc tctgccctgc    4260
ctcctgttgt cttcaagagg ctgtgtgacc tagtgaagac acattcgatg tttaagggag    4320
ccttaaagat gcacacatgc aaaatttagt catcgactgg actaaggtct atcatggcct    4380
cccttttgat cctgtctgcg ggggctcctc cagcccctcc ctccacggca cctctttctg    4440
ctggtcctat aggcccttcc ccagaaaaga ttgcttgaag cagaccagaa aaacatggcc    4500
cttgggctcc tatacactca gcttgcatct gatcctaaac atgtctcacc ttgagccttt    4560
atctaacaca ctatgtcatg gttatgtta gacactcagc agccagatgc atggaggatg    4620
gggacttttg ttctgcatca ttggtttgaa atgactggc tgaactccag tttaaagttt    4680
tcccggtgtc ccctgagatt aaccagcctt tgaccccagg gcctcctaca gccaaaaagc    4740
ctgccaccat cactgtatct ctcttttaacc tgtgtggcct ttcaagagga gtttccacta    4800
gaaaaatcag gaactcccta cagctgctca cccagcatag agagtaggtc ctgttctcct    4860
tctacagccc cggggggcgg ggcggggggg tgagaacagg aatctaaacc catcttcaag    4920
tagataccac cagcctgatg gccatcttgg cttcctgctg agccaccagg caccactctg    4980
tccttggtcc acatttatat ggctgactcc caagaccaga gtaggttaag aatattagag    5040
taagagcctg actcaggcca gagatgaccc ttgtctttat ctaaaaacac taaaatctgc    5100
atggagaggt tttgatttaa ataagtggac cacgttcctc accgagactc ctctgtgggg    5160
ggatgtgtgc tgacatctct ggttttactt cagtggagtg tcctcctggc tcatcaggaa    5220
aagatgtatg gtccctaatc aggacagagt gtgagaggct gctgctgcct ggcctgtcac    5280
cagcctggga cccctgagga catttttctca acgtcagacc tcagccatct tacttctcag    5340
aatcttagtc tgagacatga gaatggagg ccgttgcttt tctcccaaag gggaacttta    5400
gttagggggg gtgggtggtt gaatcgtgag gaacacccttt cagagaatcc tgtgccaacc    5460
agaagtggac caaactgcgc ccagggtcag cgtcacgtct tgaccaagca gctggcagca    5520
cctgacacct tagtggcgat caagtactac tgttggcaaa aggcaaggag aagcaccgtt    5580
```

```
ttgtgtcata gcaaccaggc tgtttcgttg tcttttcatg gggtcaaata tgaaaacctt    5640
gcagttctat gtagagggag aaataacgct cttctctcac ctctttcccc aacccaaact    5700
ccactgcaaa ctcatttatt cggcaaagac aaatgcttca tccctgggtc ccaggtccca    5760
ggtggtgagg gcagagcaga ggcaggtggc cctctgggct ccctggttgg cacaaggcac    5820
tgggacatct ttcccaggcc cctgggactc agctgtgctt caagtcacac acagagcctg    5880
gccctgaaga ccagggagtg attgagtctt tcctggtaaa attgtcactt tgggaaattt    5940
cacttaaaaa aaaaaaaaaa aggcggggcc cagccagctc ttttgtcaag cctgaaacta    6000
agtgtacctc acaacagacg aacgccactt ggcacccttt ctaggaagat gtcagtatta    6060
tccatgttaa gtgtcacgat gttttctgca ctgaatgaaa agaatgctc ttcatagcta     6120 tatcttaata ctgtgatttt taaaacaaaa acaaacaaac aaaccactct gatacaacta    6180
gttaactagc ttgtggtcgt gtgtctaatc accgatacct ggagttctct aatccagggt    6240
tcagtccagt gtatgttcaa agcctagctc ttgaacctgc tgggcacagc agaagcccaa    6300
ataaacaact gcagacagct gccccggggt gtgcacccct cacctgtcac tgtccctaag    6360
ctgtgtacaa tctcttccca atgtgtgaat ctgttccttc agtcactttt atttaaaaac    6420
aaaaaacaag tgccagccag gtttgactga accatgacag gaaaccgtca actttacatc    6480
agtgtttccg tcagggccac tgtgtaggcc tcttaggcta ctgttttaga gaattgttag    6540
ctatgaatta ttaccaaaga acggtggcaa tttgagctgt tctgttgagt ctccatgtca    6600
tttccaatgt cctggccaca tttctccttg gcgtgtcttc ataactccaa gatccacaat    6660
gtcattatca cattggaggc caaggggtg gggtcttaca gacacacctg aggacaggca     6720
catttccaaa gcaaggtctg aggcctgctt cctgccactt gctcactact gtccttggtg    6780
ccatcctctc agacctgggg atttgcagcc cttcacccct gtgataacag gcctaaatag    6840
gaattattga gccgatacca gcatccccac ccccacccc cagcttgttg tggatacagg      6900
gctatccagg acatcaggaa tcagggtgaa cacagaaggg caaatagaat tttctagtca    6960
catgagctga ttggttccag gcaattagaa aatggctgta acttaatctt aatttaaaaa    7020
aaaaaaaatc gagtctgttt tctccatagg agactgaact gactgtacga gtgatttata    7080
tcctgaattt atgggaaccc gtatgtttgg aacgtcctcc tgtaagctga tgaatgtaaa    7140
gagttaattt cagggtacag ttttgcctta atggttttaa aaaaaaataa actattttta    7200
aaaattaaaa aaaaaa                                                    7216
```

<210> SEQ ID NO 2
<211> LENGTH: 1769
<212> TYPE: DNA
<213> ORGANISM: Artificial sequence
<220> FEATURE:
<223> OTHER INFORMATION: PPAR gamma

<400> SEQUENCE: 2

```
caaaacacca gtgtgaatta cagcaaatct ctgttttatg ctgttatggg tgaaactctg      60
ggagattctc ctgttgaccc agagcatggt gccttcgctg atgcactgcc tatgagcact     120
tcacaagaaa ttaccatggt tgacacagag atgccattct ggcccaccaa cttcggaatc     180
agctctgtgg acctctccgt gatggaagac cactcgcatt cctttgacat caagcccttt     240
accacagttg atttctccag catttctgct ccacactatg aagacattcc attcacaaga    300
gctgacccaa tggttgctga ttacaaatat gacctgaagc tccaagaata ccaaagtgcg    360
atcaaagtag aacctgcatc tccaccttat tattctgaaa agacccagct ctacaacagg    420
```

-continued

| | |
|---|---|
| cctcatgaag aaccttctaa ctccctcatg gccattgagt gccgagtctg tggggataaa | 480 |
| gcatcaggct tccactatgg agttcatgct tgtgaaggat gcaagggttt tttccgaaga | 540 |
| accatccgat tgaagcttat ttatgatagg tgtgatctta actgccggat ccacaaaaaa | 600 |
| agtagaaata aatgtcagta ctgtcggttt cagaagtgcc ttgctgtggg gatgtctcac | 660 |
| aatgccatca ggtttgggcg gatgccacag gccgagaagg agaagctgtt ggcggagatc | 720 |
| tccagtgata tcgaccagct gaacccgag tctgctgatc tgcgagccct ggcaaagcat | 780 |
| ttgtatgact catacataaa gtccttcccg ctgaccaaag ccaaggcgag ggcgatcttg | 840 |
| acaggaaaga caacggacaa atcaccattt gtcatctacg acatgaattc cttaatgatg | 900 |
| ggagaagata aaatcaagtt caaacatatc accccctgc aggagcagag caaagaggtg | 960 |
| gccatccgaa tttttcaagg gtgccagttt cgatccgtag aagccgtgca agagatcaca | 1020 |
| gagtatgcca aaaatatccc tggtttcatt aaccttgatt tgaatgacca agtgactctg | 1080 |
| ctcaagtatg gtgtccatga gatcatctac acgatgctgg cctccctgat gaataaagat | 1140 |
| ggagtcctca tctcagaggg ccaaggattc atgaccaggg agttcctcaa aagcctgcgg | 1200 |
| aagccctttg gtgactttat ggagcctaag tttgagtttg ctgtgaagtt caatgcactg | 1260 |
| gaattagatg acagtgactt ggctatattt atagctgtca ttattctcag tggagaccgc | 1320 |
| ccaggcttgc tgaacgtgaa gcccatcgag gacatccaag acaacctgct gcaggccctg | 1380 |
| gaactgcagc tcaagctgaa tcacccagag tcctctcagc tgttcgccaa ggtgctccag | 1440 |
| aagatgacag acctcaggca gatcgtcaca gagcacgtgc agctactgca tgtgatcaag | 1500 |
| aagacagaga cagacatgag ccttcacccc ctgctccagg agatctacaa ggacttgtat | 1560 |
| tagcaggaaa gtcccacccg ctgacaacgt gttccttcta ttgattgcac tattattttg | 1620 |
| agggaaaaaa atctgacacc taagaaattt actgtgaaaa agcatttaaa aacaaaaagt | 1680 |
| tttagaacat gatctatttt atgcatattg tttataaaga tacatttaca atttactttt | 1740 |
| aatattaaaa attaccacat tataaaatt | 1769 |

<210> SEQ ID NO 3
<211> LENGTH: 3238
<212> TYPE: DNA
<213> ORGANISM: Artificial sequence
<220> FEATURE:
<223> OTHER INFORMATION: PPAR delta

<400> SEQUENCE: 3

| | |
|---|---|
| gccgcaggcc gcggcggacc tgggattaa tgggaaaagt tttggcagga gctgggggat | 60 |
| tctgcggagc ctgcgggacg gcggcagcgg cgcgagaggc ggccgggaca gtgctgtgca | 120 |
| gcggtgtggg tatgcgcatg ggactcactc agaggctcct gctcactgac agatgaagac | 180 |
| aaacccacgg taaaggcagt ccatctgcgc tcagacccag atggtggcag agctatgacc | 240 |
| aggcctgcag gcgccacgcc aagtgggggt cagtcatgga acagccacag gaggagaccc | 300 |
| ctgaggcccg ggaagaggag aaagaggaag tggccatggg tgacggagcc ccggagctca | 360 |
| atggggacc agaacacacg cttccttcca gcagctgtgc agacctctcc cagaattcct | 420 |
| cccccttcctc cctgctggac cagctgcaga tgggctgtga tggggcctca ggcggcagcc | 480 |
| tcaacatgga atgtcgggtg tgcggggaca aggcctcggg cttccactac ggggtccacg | 540 |
| cgtgcgaggg gtgcaagggc ttcttccgcc ggacaatccg catgaagctc gagtatgaga | 600 |
| agtgcgatcg gatctgcaag atccagaaga gaaccgcaa caagtgtcag tactgccgct | 660 |
| tccagaagtg cctggcactc ggcatgtcgc acaacgctat ccgctttgga cggatgccgg | 720 |

-continued

| | |
|---|---|
| aggcccgagaa gaggaagctg gtggcggggc tgactgccag cgaggggtgc cagcacaacc | 780 |
| cccagctggc cgacctgaag gccttctcta gcacatctac aacgcctacc tgaaaaactt | 840 |
| caacatgacc aaaaagaagg cccggagcat cctcaccggc aagtccagcc acaacgcacc | 900 |
| ctttgtcatc cacgacatcg agacactgtg gcaggcagaa aagggcctgg tgtggaaaca | 960 |
| gctggtgaac ggctgccgcc ctacaacgag atcagtgtgc acgtgttcta ccgctgccag | 1020 |
| tccaccacag tggagacagt ccgagagctc accgagttcg ccaagaacat ccccaacttc | 1080 |
| agcagcctct tcctcaatga ccaggtgacc ctcctcaagt atggcgtgca cgaggccatc | 1140 |
| tttgccatgc tggcctccat cgtcaacaaa gacgggctgc tggtggccaa cggcagtggc | 1200 |
| ttcgtcaccc acgagttctt gcgaagtctc cgcaagccct tcagtgacat cattgagccc | 1260 |
| aagttcgagt ttgctgtcaa gttcaatgcg ctggagctcg atgacagtga cctggcgctc | 1320 |
| ttcatcgcgg ccatcattct gtgtggagac cggccaggcc tcatgaatgt gccccaggta | 1380 |
| gaagccatcc aggacaccat tctgcgggct ctagaattcc atctgcaggt caaccaccct | 1440 |
| gacagccagt acctcttccc caagctgctg cagaagatgg cagacctgcg gcagctggtc | 1500 |
| actgagcatg cccagatgat gcagtggcta aagaagacgg agagtgagac cttgctgcac | 1560 |
| cccctgctcc aggaaatcta caaggacatg tactaaggcc gcagcccagg cctcccctca | 1620 |
| ggctctgctg ggcccagcca cggactgttc agaggaccag ccacaggcac tggcagtcaa | 1680 |
| gcagctagag cctactcaca acactccaga cacgtggccc agactcttcc cccaacaccc | 1740 |
| ccaccccac caaccccccc attccccaa ccccctccc ccaccccgct ctccccatgg | 1800 |
| cccgtttcct gtttctcctc agcacctcct gttcttgctg tctccctagc gcccttgctc | 1860 |
| cccccctttg ccttccttct ctagcatccc cctcctccca gtcctcacat ttgtctgatt | 1920 |
| cacagcagac agcccgttgg tacgctcacc agcagcctaa aagcagtggg gcctgtgctg | 1980 |
| gcccagtcct gcctctcctc tctatcccct tcaaagacat gagccatcca agaaacact | 2040 |
| acgctctctc tgggcccagc tttccaagaa gcctggcctg daccaactgc catcccagct | 2100 |
| tgtggtcacc accacagggt tcctcctcca gagagcaagt gggcagggag cctgggccgg | 2160 |
| gagccatatt cccaggctgt ctcagcccta ggcacaccc tctctgacac ttcctttctt | 2220 |
| ctcgccggcg tcctaggtca ttgtcacaga tgacccttgt gctgcctagg agatgacccc | 2280 |
| tccagatgtc ccctccagat gcggtccaac ggccccactg aagggaaggg ggtagaggca | 2340 |
| ggccggaagg agcagcggca cacttaggtc ccagggtcag aagctagaca gcgagtgggc | 2400 |
| aggccctcca tcagcacccc tcctctaccc tgtagcagca tccagactgg cagatcccag | 2460 |
| taccaggaac tggaccatag ctgttctttc ttctcctggg agatgctggc acacctgccc | 2520 |
| cccccccccc cttgcagctg ccccggtgta gccatgacac tggctcacct ctcggtcacc | 2580 |
| acagagtccc tcccattccc tccccaaggc cactggggta cagctatggc cctgttctta | 2640 |
| ggactggtga tctgtgagca ggcagggata tcctaccagg tcaccctgc cagctcacag | 2700 |
| gcagagttgc tagggttcct ctgaccctgt cctctctccc actcacttgt accagtagct | 2760 |
| ctgtggcctt ctcttctttt gcctggctgg tcacctgctc ccatctgctg cttcaagtgg | 2820 |
| cttgaaactt gctgggtgct cccatactca gccccagccc ggcagatcct gcctctaggc | 2880 |
| ccataggtga tcagcccagg ctcggctcct gccaacacag aatgctgcca gattccccgc | 2940 |
| tagcacactc cctgcccctc acctctactg atcaggtctt ggggtgttcc ttgtggggcc | 3000 |
| cacccaggct gagaatggag ctacatcacc cgccctgccc ccacctgccc agccccgccc | 3060 |
| aggtctggtg ctgaggatgc agctcctctc agggtctgaa gtctccaaat ctgaaatgta | 3120 |

```
tatttttgct aggagcccca gcttcccgtg ttttaatat aaatagtgta tacagactga    3180
cggaacttta aataaatggg aattacgtat ttaagaaaaa aaaaaaaaaa aaaaaaa      3238

<210> SEQ ID NO 4
<211> LENGTH: 6464
<212> TYPE: DNA
<213> ORGANISM: Artificial sequence
<220> FEATURE:
<223> OTHER INFORMATION: PGC1 alpha

<400> SEQUENCE: 4
gtcatgtgac tggggactgt agtaagacag gtgccttcag ttcactctca gtaaggggct     60
ggttgcctgc atgagtgtgt gctgtgtgtc agagtggatt ggagttgaaa aagcttgact    120
ggcgtcattc gggagctgga tggcttggga catgtgcagc caagactctg tatggagtga    180
catagagtgt gctgctctgg ttggtgagga ccagcctctt tgcccagatc ttcctgaact    240
tgacctttct gaacttgatg tgaatgactt ggatacagac agctttctgg gtggattgaa    300
gtggtgtagc gaccaatcgg aaatcatatc caaccagtac aacaatgagc tgcgaacat     360 atttgagaag atagatgaag agaatgaggc aaacttgcta gcggttctca cagagacact    420
ggacagtctc cccgtggatg aagacggatt gccctcattt gatgcactga cagatggagc    480
cgtgaccact gacaacgagg ccagtccttc ctccatgcct gacggcaccc ctccccctca    540
ggaggcagaa gagccgtctc tacttaagaa gctcttactg gcaccagcca acactcagct    600
cagctacaat gaatgcagcg gtcttagcac tcagaaccat gcagcaaacc acacccacag    660
gatcagaaca aaccctgcca ttgttaagac cgagaattca tggagcaata aagcgaagag    720
catttgtcaa cagcaaaagc cacaaagacg tccctgctca gagcttctca agtatctgac    780
cacaaacgat gaccctcctc acaccaaacc cacagaaaac aggaacagca gcagagacaa    840
atgtgcttcg aaaaagaagt cccatacaca accgcagtcg caacatgctc aagccaaacc    900
aacaacttta tctcttcctc tgaccccaga gtcaccaaat gaccccaagg gttccccatt    960
tgagaacaag actattgagc gaaccttaag tgtggaactc tctggaactg caggcctaac   1020
tcctcccaca actcctcctc ataaagccaa ccaagataac cctttcaagg cttcgccaaa   1080
gctgaagccc tcttgcaaga ccgtggtgcc accgccaacc aagagggccc ggtacagtga   1140
gtgttctggt acccaaggca gccactccac caagaaaggg cccagcaat  ctgagttgta   1200 cgcacaactc agcaagtcct cagggctcag ccgaggacac gaggaaagga agactaaacg   1260
gcccagtctc cggctgtttg gtgaccatga ctactgtcag tcactcaatt ccaaaacgga   1320
tatactcatt aacatatcac aggagctcca agactctaga caactagact tcaaagatgc   1380
ctcctgtgac tggcagggc acatctgttc ttccacagat tcaggccagt gctacctgag    1440
agagactttg gaggccagca agcaggtctc tccttgcagc accagaaaac agctccaaga   1500
ccaggaaatc cgagcggagc tgaacaagca cttcggtcat ccctgtcaag ctgtgtttga   1560
cgacaaatca gacaagacca gtgaactaag ggatggcgac ttcagtaatg aacaattctc   1620
caaactacct gtgtttataa attcaggact agccatggat ggcctatttg atgacagtga   1680
agatgaaagt gataaactga gctacccttg ggatggcacg cagccctatt cattgttcga   1740
tgtgtcgcct tcttgctctt cctttaactc tccgtgtcga gactcagtgt caccaccgaa   1800
atccttattt tctcaaagac cccaaaggat gcgctctcgt tcaagatcct tttctcgaca   1860
caggtcgtgt tcccgatcac catattccag gtcaagatca aggtcccag gcagtagatc    1920 ctcttcaaga tcctgttact actatgaatc aagccactac agacaccgca cacaccgcaa   1980
```

```
ttctcccttg tatgtgagat cacgttcaag gtcaccctac agccgtaggc ccaggtacga    2040
cagctatgaa gcctatgagc acgaaaggct caagagggat gaataccgca aagagcacga    2100
gaagcgggag tctgaaaggg ccaaacagag agagaggcag aagcagaaag caattgaaga    2160
gcgccgtgtg atttacgttg gtaaaatcag acctgacaca acgcggacag aattgagaga    2220
ccgctttgaa gttttggtg aaattgagga atgcaccgta atctgcggg atgatggaga     2280 cagctatggt ttcatcacct accgttacac ctgtgacgct ttcgctgctc ttgagaatgg    2340
atatacttta cgcaggtcga acgaaactga cttcgagctg tacttttgtg gacggaagca    2400 attttttcaag tctaactatg cagacctaga taccaactca gacgattttg accctgcttc   2460
caccaagagc aagtatgact ctctggattt tgatagttta ctgaaggaag ctcagagaag    2520
cttgcgcagg taacgtgttc ccaggctgag gaatgacaga gagatggtca atacctcatg    2580
ggacagcgtg tcctttccca agactcttgc aagtcatact taggaatttc tcctacttta    2640
cactctctgt acaaaaataa acaaaacaa aacaacaata acaacaacaa caacaacaat     2700
aacaacaaca accataccag aacaagaaca acggtttaca tgaacacagc tgctgaagag    2760
gcaagagaca gaatgataat ccagtaagca cacgttatt cacgggtgtc agctttgctt     2820
tccctggagg ctcttggtga cagtgtgtgt gcgtgtgtgt gtgtgggtgt gcgtgtgtgt    2880
atgtgtgtgt gtgtacttgt ttggaaagta catatgtaca catgtgagga cttggggca    2940 cctgaacaga acgaacaagg gcgaccccctt caaatggcag catttccatg aagacacact   3000
taaaacctac aacttcaaaa tgttcgtatt ctatacaaaa ggaaaataaa taaatataaa    3060
ttaaaaggaa agaaaactca caaaccaccc taaaatgaca ctgctgatgc ctgttgtcag    3120
cctccggtac cgtcttttca gaaagtgcaa accccagaaa gtgcaaaacc aacctgcagc    3180
aagctctctc tctctcttaa tgtaatcatt acgtgacaat cccgaagaca ctacaggttc    3240
catagaactc atatccacct ctctctctct ctctctctct ctctctctct ctctctctct   3300
cctctctcct ctctcctctc tccctcccctt ctttgccatt gaatctgggt gggagaggat    3360
actgcaggca ccagatgcta aacttttccta acatttgaa gttctgtag tttgtccttt     3420 gtcctgacac ctatgtatat gttcaaaatg ttgatcttcc actgcagatt ttgaaaagcc    3480
ttgttattgg tcaagcgggg agtgtgttca gtggctcctt ctgaggagca gacgcggtgt    3540
tacatgagta ctgagagttg agtagaactc tctggatgtg ttcagatagt gtaattgcta    3600
cattctctga tgtagttaag tatttacaga tgttaaatgg agtattttta ttttatgtac    3660
atactctaca actatgttct tttttgttac agctatgcac tgtaaatgca gccttctttt    3720
caaaactgct aaattttttct taatcaagaa tattcaaatg taattatgag gtgaaacaat    3780
tattgtacac taacatatt agaagctaaa cttactgctt atatatattt gattgtaaaa     3840
aaaaaaaaaa acaaaaccaa caaaacaaaa gacagtgtgt gtgtgtgtgt ccgttgagtg    3900
caagtccaac aaaatggcgc ttcacgcaca tccatccctt cttaggtgag cttcaatcta    3960
agcatcttgt caacaacaac aaaaatccta ggcccctcaa ggtattaacc acttctgcaa    4020 tattttttcca catttcttg ttgcttgttt tctttgaag ttttatacac tggatttgtt     4080
aggggaatga aattttctca tctaaaattt ttctagacaa tatcatgatt ttatgtaaag    4140
tctctcaatg gggaaccatt aagaaatgtt tttattttct ctatcaacag tagatttgaa    4200
actagaggtc aaaaaaaatc tttttaaaat gctgtttttgt tttaattttt gtgattttaa   4260
tttgatacaa aatgctgagg taataattac agtatgattt ttacaatagt caatgtgtgt    4320
ctgaagacta tctttgaagc cagtatctct ttcccttggc agagtatgat gatggtattt    4380
```

```
aatctgtatt ttttacagtt atacatcctg taaaatactg atatttcatt cctttgttta    4440
ctaaagagac atatttatca gttgcagata gcctatttat tataaattaa gagatgatga    4500
aaataataag gtcagtggag actttctacc cagggtgcat ggcagttgtc aggctggagt    4560
gtaccttctt cgtttgggaa actcagctct cgcagaagca gtgttccatc tttcactagc    4620
atggcctctg atacgaccat ggtgttgttc ttggtgacat tgcttctgct aaatttaata    4680
ttaataataa taaatgtcag aaaaaaaacc ctccatttg agcatcagga tttcatctga     4740
gtatggagtc gctgccatgg gagtcactaa actttggagt atgtatttca tttccaaatt    4800
gagatgcatt tactgtttgg ctgacatgaa ttttctggaa gatatgatag acctactact    4860
taaccgtttt tgtttgtttt tttttctttg ttgttgttgt tttgttttt gttttttgt       4920 ttttctctct cacccaacac tatcttacaa aatgggtttc acccccaggc caatgcagct    4980
aattttgaca gctgcattca tttatcacca gcatattgtg ttctgagtga atccactgtc    5040
tgtcctgtcg aatgcttgct caagtgtttg gcttattatt tctaagtaga tagaaagcaa    5100
taaataacta tgaaataaaa aagaattgtg ttcacaggtt ctgcgttaca acagtaacac    5160
atctttaatc cgcctaattc ttgttctgta ggataaatgc aggtatttta actctttgtg    5220
aacgccaaac taaagtttac agtctttctt tctgaatttt gagtatcttc tgttgtagaa    5280
taataataaa aagactatta agagcaataa attattttta agaaatcaat atttagtaaa    5340
tcctgttatg tgtttaagga ccagatgcgt tctctatttt gcctttaaat ttttgtgatc    5400
caactttaaa aacatacgtt gtcttgtttg ccctggatca tggacatgac taaaattttg    5460
tggtttcttt tcttacttat caaaagacaa cactacagat ttcatgttga ggattcattg    5520
agctctcacc ctctggcctg acaaatcttg ttaccatgaa gatagttttc ctccgtggac    5580
ttcaaattgc atctaaaatt agtgaagctt gtgtatctta tgcagacact gtgggtagcc    5640
catcaaaata taagctgtaa gctttgttcc tttcattttt ttttttttac ttcttttggg    5700
agagaatatt tccaacaaac acatgcaccc caccaacagg ggaggcaaat ttcagcatag    5760
atctataaga ctttcagatg accatgggcc attgccttca tgctgtggta agtactacat    5820
ctacaatttt ggtacccgaa ctggtgcttt agaaatgcgg ggttttatt aaaaaaaaa      5880 aaaagaaatg tagcagaata attctttttag tgcagcaact cagttttgt aaaggactct    5940 gagaacactt gggctgtgaa cattcaaagc agcagagagg gaacctggca ctattggggt    6000
aaagtgtttg ggtcagttga aaaaaaggaa acctttcat gcctttagat gtgagctaac     6060
agtaggtaat gatcatgtgt ccctttttga tggctgtacg aagaacttca atcactgtag    6120
tctaagatct gatctataga tgacctagaa tagccatgta atataatgtg atgattctaa    6180 atttgtaccct atgtgacaga catttcaat aatgtgaaaa ctgcagattt gatgagcta     6240 ctttaagatt tgtaggtgaa agtgtgctac tgttggttga actatgctga agagggaaag    6300
tgagtgatta gtttgagccc ttgctggctc ttttccacct gccaattcta catgtattgt    6360
tgtggtttta ttcattgtat gaaaattcct gtgatttttt tttaaatgtg cagtacacat    6420
cagcctcact gagctaataa agggaaaaga atgtttcaaa tcta                      6464
```

<210> SEQ ID NO 5
<211> LENGTH: 4331
<212> TYPE: DNA
<213> ORGANISM: Artificial sequence
<220> FEATURE:
<223> OTHER INFORMATION: CPT1a

<400> SEQUENCE: 5

```
gtcggtgagc ctggcctcgc ccgccccggc ccggactccg ctcgctcatt ccgccgccgc    60
cgtctgcaga ctcggtcacc actcaagatg gcagaggctc accaagctgt ggccttccag   120
ttcacagtca cccctgatgg catcgatctc cgcctgagcc atgaagccct caaacagatc   180
tgcctgtcag gctgcactc ctggaagaag aagttcatcc gattcaagaa tggcatcatc    240
actggtgtgt tccccgcgag tccctccagc tggcttatcg tggtggtggg tgtgatatca   300
tccatgcata ccaaagtgga cccctccctg ggcatgattg caaagatcaa tcggacccta   360
gacaccactg gccgcatgtc aagccagacg aagaacatcg tgagtggcgt cctctttggc   420
acagggctct gggtggcgat catcatgact atgcgctact cgctgaaggt gctgctctcc   480
taccatggct ggatgtttgc agagcacggc aaaatgagcc gcagcaccag aatctggatg   540
gctatggtca aggtcttctc gggtcgaaag cccatgttgt acagcttcca gacgtctctg   600
ccgcgcctgc ctgtcccagc tgtcaaagat accgtgagca ggtacctgga gtctgtgagg   660
ccactgatga aggagggaga cttccaacgc atgacagcac tggcccagga ttttgctgtc   720
aaccttggac ccaaattgca gtggtatttg aagctaaaat cctggtgggc cacaaattat   780
gtgagtgact ggtgggagga atacatctac ctgcggggcc gagggccgat catggttaac   840
agcaactact acgccatgga gatgctctac atcaccccaa cccatattca ggcagcgaga   900
gctggcaaca ccatccacgc catactgctg tatcgtcgca cggtagaccg tgaggaactc   960
aaacctattc gtcttctggg atctacaatt cccctctgct ctgctcagtg ggagcgactc  1020
ttcaatactt cccgcatccc tggggaggag acagacacca tccaacacgt caaggacagc  1080
aggcacattg tcgtgtacca cagaggccgt tacttcaagg tctggctcta ccatgacggg  1140
aggctgctga ggccccgtga gctggagcag cagatgcagc agatcctgga tgacacctca  1200
gagccgcagc ccggggaagc caagcttgcc gccctcactg ccgcagacag agtgccctgg  1260
gcgaagtgtc ggcagaccta ttttgcacga ggaaaaaata gcaatctct ggatgcggta   1320 gaaaaggcag cattcttcgt gacgttggac gaatcggaac agggatatag agaggaggac  1380
cctgaggcat ctattgacag ctatgccaaa tctctgctgc atggtagatg tttcgacagg  1440
tggtttgaca agtccatcac ctttgttgtc ttcaaaaaca gcaagatagg cataaacgca  1500
gagcattcct gggcggacgc gcccatcgtg ggccatctgt gggagtatgt catggccacc  1560
gacgtcttcc agctgggcta ctcagaggat ggacactgta aaggagacaa gaaccccaac  1620
atccccaaac ccaccaggct acagtgggac attccaggag aatgccagga ggtcatagag  1680
acatccctaa gcagtgccag ttttttggca aatgatgtgg acctgcattc cttcccattt  1740 gcacccttig gcaaaggctt gatcaagaag tgccggacga gtcccgatgc cttcatccag  1800
ctggcactgc agctcgcaca ttacaaggac atgggcaagt tctgcctcac gtatgaggct  1860
tccatgactc ggctcttccg agaggggagg acagagactg tacgctcctg cactacggag  1920
tcctgcaact ttgtgctggc catgatggac cccacaacaa cggcagagca gaggttcaag  1980
ctgttcaaga tagcttgtga aaagcaccag cacctgtacc gcctcgccat gacgggcgct  2040
ggcatcgacc gccacctctt ctgcctctat gtggtgtcca gtatctggc agtcgactca   2100 cctttcctga aggaggtact gtctgagcca tggaggttgt ccacgagcca gactcctcag  2160
cagcaggtgg aactgtttga cttttgagaaa taccctgact atgtgtcctg tggcggggc   2220 tttgggccgg ttgctgatga cggctatggt gtttcctaca ttattgtggg agagaatttc  2280
atccacttcc atatttcttc caagttctct agccctgaga cagactcaca ccgctttggg  2340
aagcacttga gacaagccat gatggacatt atcaccttgt ttggcctcac cgccaattcc  2400
```

```
aaaaagtaac tgtcggagcc gcacggaagg aaaatggact ctagtgatac aaaccaaatg    2460
aataggtgtt gctcctgacc ataggacagg cagaaaattg ttcttataaa actcagtttt    2520
ccttccagaa ggtttaccgt cggtctccct agaacaaccg taggctccac cgtttgactt    2580
gtgaccctac tacatccaga gatgccttgg ctccaggaat attgggcaca gtcccccgaa    2640
gtcttttgaa tcggctccta atggataaag ggatttaaat gctggtgaat ccctggattt    2700 tggggggttgt atcaatatgt gttggaggtg acagacttcc tcagtggtga ccctgtggat    2760
acttgggact tgacttcacc caggcagtga gagcatcacc ttgtggaaag agaaagtggc    2820
ttcagagcca gtggaggtaa cagctctagc taacacacct gtaacacact aatggaatgg    2880
ttaggcctgg ggattaaggt tctgctatga atgacagcca ccatcgcttt gggagtccac    2940
atttgactcc acatttcctg gaagcaggat accacctcct cagtgccacc ttcgaaaccc    3000
agtgccttaa cgatgggagc ccattggcaa gtggggccat agagaaggct tagcatgtga    3060
agcctttggg tggatatgtg agggtgctgc ttccccctcac aagttcctgc atagagatgt    3120
ccctaagtaa gcacttcccc caccctagaa gatgaggtcc ctggtggagg gagcgatgca    3180
gaatctcatt ggccaccagt tccattaagc aacaaaataa cagatgtgtc cacagaggga    3240
agtgaggggc ttggtagtca aaggctacca agttggacac cagctggaga gtgtggcagc    3300
cattggcaag gagagtgaga ccctggtcac tgagtcaggc atactgacac aggcagccaa    3360
agccttgtca tggcagccag gagatagaga tcctggcaga tacaccaacg ggctcatctt    3420
ctaatcccac ccagtcagat tccaaccaga gcaaattcga tagaaggcta ggtcattttg    3480
gtgacagact cgggggtctc aagtaatggg tgctttgtac ccaaatacca tccctctgtg    3540
agagtgcctt tcttgacaac atccaataga ctgtaaagca actccgtttg gtattccatg    3600
taaacatagc ataatggagt ggcctcccct acctgttacc atcctgtcct gacaagttta    3660
gctcttcgtg ttttaaatca tgtatttatt ttccagtgcc cctttggcct tgcttgattc    3720
ctactcgtgt gctagctgta acagaagtga gggtggggtg gccagaagta cagagaggtg    3780
ctggctgaac agctcatgcg tgttttataa gtatccatga atacaaaaaa aagaatcaca    3840
cctacaaggg ccaaagtttt tttcctacta aaaacaagaa aacaaaaggc aacataaata    3900
tatagcagag acaactgtaa gtcaaagccg cctgaccgcg ctcttaggac tacttgctaa    3960
cctctgttac tcgagtatt cctgctagta cccaagtgtg acattcctct ctcaggtctc    4020
cagtgtcctt ccttgctgct cctgagcagt taccaatgca attttttact ccttccaagg    4080
cagaagagtg ggctttcact gtaagtgttc aaaggaggag gtaagactac tatgtattta    4140
atgtggaaca aaacatagtc ttaccgcagc caaggttcga atttggtttt ctaatctgtc    4200
cattgcatgt aaataccata tgctgtttgg atataaatct tagaaatgca tgtgtgaacg    4260
aatatagctg accattaata aaacattaat cccgcctact aaaaaaaaaa aaaaaaaaa    4320 aaaaaaaaa a                                                         4331

<210> SEQ ID NO 6
<211> LENGTH: 2894
<212> TYPE: DNA
<213> ORGANISM: Artificial sequence
<220> FEATURE:
<223> OTHER INFORMATION: CPT1b

<400> SEQUENCE: 6
tgaaggacgt ggggacatgg gccagagagg ccagacccat acaccgacag aagcaaacct      60
gagctgtgct gaataaaccc caggatggcg gaagcacacc aggcagtagc tttccagttc     120
```

```
actgtgaccc cagacggggt cgacttccgg cttagtcggg aggctctgag acacatctac    180
ctgtctggaa tcaactcctg gaagaaacgc cttattcgaa tcaagaatgg catccttagg    240
ggtgtgtacc ctggcagccc caccagctgg ctggttgttg tcatggcaac agttggttcc    300
aactactgca aggtggacat ctccatggga ctggtcgatt gcatccagag atgcctcccg    360
gaaaggtatg ccactttgg gaccccacag acagaggcac ttctcagcat ggtcatcttc     420
tccaccggag tctgggcgac aggcattttc ttcttccgac aaaccctgaa gctgctgctc    480
tcctaccacg ggtggatgtt cgagatgcac agcaagacca gccatgccac caagatctgg    540
gctatctgtg tccgtctcct gtccagccgg cggcccatgc tctacagctt ccaaacgtca    600
ctgcctaagc ttcctgtccc cagcgtgcca gccacaattc accggtactt ggattctgtg    660
cggcccttat tggatgatga agcatattac cgcatggaga cattggccaa ggaattccag    720
gacaagactg cccccaggct gcagaaatac ctggtgctca agtcatggtg ggcaactaac    780
tatgtgagtg actggtggga agaatatgtc tacctccgaa gcaggagccc cctcatggtg    840
aacagcaact attatgccat ggattttgtg cttattaaga acacaaatgt gcaagcagcc    900
cgtctaggca atgccgttca cgccatgatc atgtatcgcc gcaaactgga ccgtgaagag    960
atcaagccgg tcatggcact gggtatggtg cccatgtgct cctaccagat ggagaggatg   1020
ttcaacacta cacgcatccc aggcaaagag acagacttgc tacagcacct ctcagagagc   1080
aggcacgtgg ctgtctacca caaaggtcgc ttcttcaagg tctggctcta tgagggctcg   1140
cgcctgctca gccccgaga cctggagatg cagttccaga gaatcctcga cgacccttcc    1200
ccacctcagc ctggggagga aagctggca gccctcaccg caggaggaag ggtagagtgg    1260
gcagaggcac gtcagacctt cttcagctct ggcaagaaca agatgtctct ggacgccatc   1320
gaacgtgctg cttctctttgt gaccctggat gaagattctc attgctacaa ccctgacgat   1380
gagaccagtc ttagcctcta cggcaaagcc ttgctccatg gcaactgcta taacaggtgg   1440
tttgacaaat ctttcaccct tatctcctgc aagaatggcc tgttaggcct caacaccgaa   1500
cactcgtggg cagacgcgcc catcattggg cacctctggg agtttgtcct gggcactgat   1560 accttcacc tgggctacac ggagacagga cactgtgtgg gtgagccaaa caccacgttg    1620 ccacccctc agcggctgcc gtgggacatt cccgagcagt gccgggaagc catcgagaac   1680
tcgtaccaag tagccaaggc actggccgat gacgtggagc tctactgctt ccagttctta   1740 cccttttggca aaggtcttat caagaagtgt aggaccagcc ccgacgcttt tgtgcagatt   1800
gccctacagc tggctcattt ccgggacaaa ggcaagttct gcctgactta cgaggcctcg   1860
atgacaagaa tgttccgaga ggggcggact gagactgtgc gttcctgtac caacgagtcc   1920
gcagcctttg tgcaggccat gatgaagggg tcccataaga acaagacct ccaagatctc    1980 ttccggaaag cctccgaaaa gcaccaaaac atgtaccgcc tagccatgac aggggctggg   2040
atcgaccggc acctcttctg cctttacatc gtctccaagt acttaggagt tagctctcct   2100
ttcctggctg aggtactttc tgaaccctgg agcctctcca ccagccagat cccccagttc   2160
cagatctgca tgtttgaccc caaaacagtat cccaatcatc tgggtgctgg aggtggcttt   2220
ggtcccgtgg cggatgatgg ctacggggtc tcttacatga tcgcaggaga aaacaccatg   2280
ttcttccaca tctccagcaa atactcaagt tcagagacga acgcccagcg ctttgggaac   2340
cacatccgcc aagcactgtt ggacatcgcc gaacttttca aaatttccaa gacagacagc   2400
tgaggaaaag agatacccca gctgccctct ggtcccacc tggtggaaga gaggcctgt    2460 ggccagctca caggcataag gggtggcgtg cacacacgcc cagttcggag aacagctctt   2520
```

-continued

| | |
|---|---|
| gaggcagtgc tccccggagg aggcagtgct ccctgggcag atactgctcc tctagggccc | 2580 |
| ccgctggagg tgggattgga gcagcagggg aatttgatt tttttttttt tttttggct | 2640 |
| tggtagatgt taataaaaat aaggctgtat aattcttact tggctgttag gtgcctatgt | 2700 |
| ttttgttaga gaacgataag gcccttcct gccccagctc agcctaggat ggaggcgatg | 2760 |
| gaaggggtcg gagaatgttc ataatgggct tcttacctgc tttgaaatgg gtgctcttct | 2820 |
| tgaataatgc ggacttggag agcgctgtcc aacctctcat gtgcacttgg aataaattct | 2880 |
| tactttagaa cctt | 2894 |

<210> SEQ ID NO 7
<211> LENGTH: 1892
<212> TYPE: DNA
<213> ORGANISM: Artificial sequence
<220> FEATURE:
<223> OTHER INFORMATION: ACD1

<400> SEQUENCE: 7

| | |
|---|---|
| gccgccgtcc atcccgccat ggctgcgcgc ctgctcctcc gctccctgcg cgtcctgagc | 60 |
| gcccgctcgg cgccacgccc gctgccctcc gcccgatgtt ctcattctgg agcagaagcg | 120 |
| cgtctagaaa ctccttctgc taaaaaatta actgacattg aatcaggag aatcttttcc | 180 |
| tcggagcatg acattttccg ggagagtgta aggaagtttt tccaagaaga agtgattcct | 240 |
| caccacacag aatgggagaa agctggagaa gtgagtagag aggtctggga aaaagctggc | 300 |
| aagcagggct tgcttggcat caacatcgca gagaaacatg gcggcattgg tggggacttg | 360 |
| ctctcaacag cagttacttg ggaagagcaa gcgtactcca attgcacagg ccctggcttc | 420 |
| agcctccact cagatattgt catgccctat attgcgaatt acggcacaaa gaacagatc | 480 |
| gagaagttca tcccccagat gacggcgggc aagtgtatcg gtgccatagc catgacagag | 540 |
| cctggggctg gaagtgactt acaaggagta agaacgaacg ccaaaagatc tgggagtgat | 600 |
| tggattctca atggaagcaa ggtgttcatc actaatggct ggttaagtga tctcgtgatc | 660 |
| gtcgtggccg tcaccaaccg tgaagctcga tcgcctgccc atggcattag cctctttttg | 720 |
| gtggaaaacg gaatgaaagg atttatcaag gccggaagc tgcataagat gggaatgaaa | 780 |
| gctcaggaca cagcagaact attctttgaa gatgtccgat tgccagctaa tgccttactt | 840 |
| ggagaagaga ataaaggctt ctactacctc atgcaagagc ttccacagga aaggctctta | 900 |
| attgctgagt tggcgatttc tgcctgtgag ttcatgtttg aagaaccag gaactacgtg | 960 |
| aagcaaagaa aagcttttgg gaaaacagtt gcacacatac agacggtgca gcataaacta | 1020 |
| gcagaattaa agacacacat atgtgtcacc agagcttttg tggacagctg tctgcagttg | 1080 |
| catgaaacca aacgtctgga ctccggttct gcttccatgg caaaatactg ggcatctgaa | 1140 |
| ttacaaaaca gtgtagctta tgaatgtgtg caactccacg gaggctgggg gtacatgtgg | 1200 |
| gagtacccga ttgcaaaagc ttacgtggat gctcgggtgc agccgatcta cggtggtacc | 1260 |
| aacgaaataa tgaaagagct gatcgcaaga cagatcgtca gtgacagcta gacatctgcc | 1320 |
| tacatcctgg aatcctatta catgcagcta atgcggattc taatctactt gagataaagt | 1380 |
| gtaacctgga aaaggggggg aaatggtaaa gctggtttta tgtatgattg ttacagagaa | 1440 |
| agaaataaaa tagaattcta agattaaca cagggagaga gaattttg agcccaagag | 1500 |
| tctaaagttt tgtcatgaaa ggtataacct ttttcatgc atatacagtg aatataaaag | 1560 |
| attttctaac tgaagagcct tttaatgtct tacttgtctt tcaaattctg aagagcataa | 1620 |
| gttggctttc attcttaaag ttgaggcaga atttaatatt aataatactt acaagacttt | 1680 |

| | |
|---|---|
| ggaaaggtca aataattgta acttatatga agtcatttca gctactttt gctccatatt | 1740 |
| cccccaggac attggttccc accatgttac ccccaacccc atgttttta aagtaatgaa | 1800 |
| cagaacccctt cagaaaaaag tggaccgtac tgtatataat gcacatagag gcaattgtgt | 1860 |
| atcaatatta aaaataaagt aaaacttaaa gc | 1892 |

<210> SEQ ID NO 8
<211> LENGTH: 3810
<212> TYPE: DNA
<213> ORGANISM: Artificial sequence
<220> FEATURE:
<223> OTHER INFORMATION: ACS1

<400> SEQUENCE: 8

| | |
|---|---|
| ctctttgcat atgcaacgag cgccagcccg gggtgcgcgt ccaggactgc ggctcaacag | 60 |
| acgctgctca gccggcgccc gggaaacgtc gctgcggttg tggccgcggt cgcgggctcg | 120 |
| gacgaggagg cggcggcaga gcgggaggct gagccggcag caggcggtcg tccccgtctc | 180 |
| gcagggcggc cccagcagct gcgtcagggt cctgaggagg tggcgctggg caggagccgc | 240 |
| tctgaggagc agccaggcct gcgtgggtcg gagcccgcga ttctcattga aatctgttaa | 300 |
| ttctattttt tgaacactta tgaataacca cgtatcttca acaccatcaa ccatgaagct | 360 |
| aaaacaaacc atcaaccccca tacttttata tttcatacat tttataatat cactctatac | 420 |
| tattttaaca tacatcccat tttattttt gtgtgagtca aaacaagaga aaccaaacca | 480 |
| aattaaagca aaacctgtca gttccaaacc ggactctgca tacagatcta tcaacagtgt | 540 |
| ggatggcttg gcttcagtgc tgtatcctgg ctgcgataca cttgataaag tctttatgta | 600 |
| tgcaaaaaac aaatttaaaa acaaaagact attgggaaca cgtgaaattt taaatgagga | 660 |
| agatgaaata cagccaaatg gaaaaatttt taaaaggtt attctggggc actataattg | 720 |
| gctttcctat gaagatgtct tcatccgagc ccttgacttt ggaaatgggt tacaaatgtt | 780 |
| gggccagaaa ccaaaggcca acatcgccat ctttctgtgag accagggctg agtggatgat | 840 |
| cgctgcacag gcgtgttta tgtataactt ccagcttgtt acactgtatg ctactctggg | 900 |
| aggtccagcc attgttcatg gactgaatga gacagaggtg accaacatca ttactagcaa | 960 |
| agaactcttg caaacaaagc tgaaggatat agtctcttg gtcccacgtc tgcggcatat | 1020 |
| cattactgtt gatgggaagc ctccaacctg gtctgagttc cccaaaggtg tcattgtaca | 1080 |
| caccatggct gcagtgcagg ctctaggagt gaaggccaac gtggaaaaga agctcacag | 1140 |
| caaaccactg ccctcagata ttgcagtaat catgtacaca agtgggtcca caggaattcc | 1200 |
| aaagggagtc atgatctcac acagcaacat cattgcttct ataacgggga tggcgagaag | 1260 |
| gattccaaga ctgggagagg aagatgtgta tattggctac ttgcccctgg cacatgttct | 1320 |
| agaattaagt gctgagcttg tgtgtctttc tcatggatgc cgaatcggct actcttcacc | 1380 |
| acagacatta gcagatcagt cttcaaaaat aaaaaaagga agcaaaggag acacatccgt | 1440 |
| gctgaagcca acactgatgg cagctgttcc ggaaatcatg gatcggatct acaaaaatgt | 1500 |
| catgaataaa gtgaatgaaa tgagtgcttt tcaacgaaac ttgttttatt tggcatataa | 1560 |
| ttataagatg gaacagattt caaaagggtg tagtactcca ctgtgtgacc gctttgtttt | 1620 |
| ccggaatgtc cgaaggctgc tgggtggaaa tattcgcctt ttactgtgtg gtggtgctcc | 1680 |
| gctttctgca acaacgcagc gattcatgaa tatctgtttc tgctgtcccg ttggtcaggg | 1740 |
| gtatggactc acagaatcta ctggggctgg aacaattaca gaagtgtggg actcaaatac | 1800 |
| cggcagagtg ggagcaccat tagtttgctg tgaaatcaaa ttaaagaact gggaggaagg | 1860 |

```
tggctatttt aatactgaca aaccacatcc cagaggtgaa attcttattg gtggccaaaa      1920
tgtgacaatg gggtactaca aaaatgaagc aaaaacaaag acagatttct ttgaagatga      1980
aaatggacag cggtggctgt gcactggaga tattggagag tttgaccctg acggctgtct      2040
gaagatcatt gaccgtaaaa aggaccttgt gaaactacag gcaggagagt acgtttctct      2100
cgggaaagta gaggcagctt tgaagaacct cccactgata gataacattt gtgcgtatgc      2160
aaacagctac cattcttacg taattgggtt tgttgtgcca aatcaaaagg aacttacaga      2220
gctagctaga acaaaaggat ttaaaggaac ttgggaagag ctgtgtaaca gcagcgagat      2280
ggaaaatgag gtccttaaag tgctttctga agctgctatt tcagcaagtc tggaaaagtt      2340
tgaaattcca ctaaaaatac gtttgagccc tgacccatgg actcccgaaa ctggtctggt      2400
gacagatgcc ttcaagttga aacgtaaaga gcttaaaaca cactaccagg cagacattga      2460
gcggatgtat ggaagaaaat aattagtttt ggcattggtt tgctacagcg agctcagatc      2520
aaataggaaa atactgaaa tgtatgtctc gggccgaggc aaactccatt cctcatatta      2580
aatcccggct gttacttctc actacgtcac cattttaac tgacaggatt agtaaagtat      2640
taagacagca aactcgtgtc tgtctgttcc ttcccctgct ccagtttgct tctggcatct      2700
gtgactgtgc ttgtcaacag gagacttttt cagaatcgta ctggggaagc agcgatttta      2760
cagcctcaag ttttaaaca tgatttatat gttctgtaca gttgttcagt ttgtaacttt      2820
ttaaagtttg gatgtataga aggataaata ggaaatataa aaattggtta tttgggggggc      2880 ttttttactt attgtattta aaaataaaag ggtatcaatg tgaaattatg tacatttttaa      2940 atgcttatga atcaagtcat tgttgaacaa aagatttgtt gctgtgtaat tattgtcttg      3000
tatgcatttg agagaaataa atatactcag acttatgttt taagaaattt cgaatatatg      3060
cctgacactg ttgggttat atacttgctt tttctgttgg ggaaaacagt ttgcttggca      3120
ctgcattgaa gtgaaagagc aagtaggggt acataacagt tcactcacag agcagctcac      3180
cacagagcag cggtggccat gggtgtggtg gtgggtgagg ggaaccaggg ctctggagtt      3240
tcgctcacat cacaaagtac ttgtttagag acatcctagg acagtgttct ctgtgttctc      3300
gtatgttgtg tgttggacag ttttgtccct tgttgaaattt aactcttacc tttgagaaa      3360 ctttgtaaag gaggggaagt gtgttaatac taggagccga aaattacca tggttgctgg      3420 agagcatttg tgtctgcctg atggcttgcc ttcagaatga ttgtgttaaa atattttat      3480 aaaatgatt taagtcacgt gtgtatgtgt gcatgcagtg attaaagatg tcagaagggg      3540
gcgtctgatc ctctgaaatg agttaaaagc tgtggtgaac caaattctac tttctgtaag      3600
actggagcat gctcttaaat gctgagctgt cgttccagca ctctttcaaa ggatttgttt      3660
ttctttttta aaaatagaa tgtaagtaag cttcaatgct tttggaaaga tactaacaat      3720
tgtgacttga aatgtcagct taaaaggcag tgtctcacca gtacagtaat ggctgattga      3780
acagcaaata aagctggtta gtccgcatca                                       3810

<210> SEQ ID NO 9
<211> LENGTH: 1644
<212> TYPE: DNA
<213> ORGANISM: Artificial sequence
<220> FEATURE:
<223> OTHER INFORMATION: UCP1

<400> SEQUENCE: 9
aagtgccggg caatctgggc ttaacgggtc ctccctgccc gagcaagagg aagggacgct        60 caccttgag ctgctccaca gcgccgcctc tgcactggca ctacctagcc caggtggctc       120
```

```
tgcaggagtc cgaagtcgcg ggtttcgtgc ccgcatcagg caacagtgcc actgttgtct    180
tcagggctga gtccttttgt tcttgcactc acgcctctct gccctccaag ccaggatggt    240
gaacccgaca acttccgaag tgcaacccac catgggggtc aagatcttct cagccggagt    300
ttcagcttgc ctggcagata tcatcacctt cccgctggac actgccaaag tccgccttca    360
gatccaaggt gaaggccagg cttccagtac cattaggtat aaaggtgtcc tagggaccat    420
caccaccctg gcaaaaacag aaggattgcc gaaactgtac agcggtctgc ctgcgggcat    480
tcagaggcaa atcagctttg cctcactcag gattggcctc tacgactcag tccaagagta    540
cttctcttca gggagagaaa cacctgcctc tctcggaaac aagatctcag ccggcttaat    600
gactggaggt gtggcagtgt tcattgggca gcctacagag gtcgtgaagg tcagaatgca    660
agcccagagc catctgcatg ggatcaaacc ccgctcacg  ggacctaca atgcttacag    720 agttatagcc accacagaaa gcttgtcaac actttggaaa gggacgaccc ctaatctaat    780
gagaaatgtc atcatcaatt gtacagagct ggtaacatat gacctcatga agggggccct    840
tgtaaacaac aaaatactgg cagatgacgt cccctgccat ttactgtcag ctcttgttgc    900
cgggttttgc accacactcc tggcctctcc agtggatgtg gtaaaaacaa gattcatcaa    960
ctctctgcca ggacagtacc caagcgtacc aagctgtgcg atgtccatgt acaccaagga   1020
aggaccgacg gccttttttca aagggtttgt ggcttctttt ctgcgactcg ggtcctggaa   1080
cgtcatcatg tttgtgtgct ttgaacagct gaaaaaagag ctgatgaagt ccagacagac   1140
agtggattgt accacataag caacttggag gaagagatac tgaacatcat tgggcttcta   1200
tgctgggaga ccacgaataa aaccaaccaa agaaatcaaa tgaacagctc cgttgacttt   1260
atttacatta caagatcatt tccagtagag agttttgaaa cctctttaa tttttttaa   1320 agggaaaact aacacataca catagttttt attcttactg tcttaaagac agaagagcat   1380
agcattcact aatattttga gaaataata cctatataa gtcctgtatt taactggtct   1440
ttggggagag gtgggagtgt atgactgggt ataaagaatt ctgattacag ctcaaactag   1500
tgggaaggaa aaattagtcc aaaacccttt acatcgataa acactttaaa aagaaagct   1560 atcaaaaaaa tattgccatt tcatcttatt tattgaccac agttcacagc taatatactc   1620
aataaagtat tgctaattcc atct                                         1644
```

<210> SEQ ID NO 10
<211> LENGTH: 4299
<212> TYPE: DNA
<213> ORGANISM: Artificial sequence
<220> FEATURE:
<223> OTHER INFORMATION: SREBP1

<400> SEQUENCE: 10

```
agtttccggg gaacttttcc ttaacgtggg cctagtccga agccgggtgg gcgccggcgc     60
catggacgag ctggccttcg gtgaggcggc tctggaacag acactggccg agatgtgcga    120
actggacaca gcggttttga cgacatcga agacatgctc cagctcatca acaaccaaga    180
cagtgacttc ccgggcctgt ttgacgcccc ctatgctggg ggtgagacag ggacacagg    240 ccccagcagc ccaggtgcca actctcctga gagcttctct tctgcttctc tggcctcctc    300
tctggaagcc ttcctgggag gacccaaggt gacacctgca cccttgtccc ctccaccatc    360
ggcacccgct gctttaaaga tgtacccgtc cgtgtccccc ttttcccctg gcctgggat    420 caaagaggag ccagtgccac tcaccatcct acagcctgca gcgccacagc cgtcaccggg    480
gaccctcctg cctccgagct tccccgcacc acccgtacag ctcagccctg cgcccgtgct    540
```

```
gggttactcg agcctgcctt caggcttctc agggacccct tccaggaaaca ctcagcagcc   600
accatctagc ctgccgctgg ccccctgcacc aggagtcttg cccaccccctg ccctgcacac  660
ccaggtccaa agcttggcct cccagcagcc gctgccagcc tcagcagccc ctagaacaaa   720
cactgtgacc tcacaggtcc agcaggtccc agttgtactg cagccacact tcatcaaggc   780
agactcactg ctgctgacag ctgtgaagac agatgcagga ccaccgtga agactgcagg    840
catcagcacc ctggctcctg gcacagccgt gcaggcaggt ccctgcaga ccctggtgag     900
tggagggacc atcttggcca cagtaccttt ggttgtggac acagacaaac tgcccatcca   960
ccgactcgca gctggcagca aggccctagg ctcagctcag agccgtggtg agaagcgcac  1020
agcccacaat gccattgaga agcgctaccg gtcttctatc aatgacaaga ttgtggagct  1080
caaagacctg gtggtgggca ctgaagcaaa gctgaataaa tctgctgtct gcgcaaggc   1140
catcgactac atccgcttct gcagcacag caaccagaag ctcaagcagg agaacctgac   1200
cctacgaagt gcacacaaaa gcaaatcact gaaggacctg gtgtcagctt gtggcagtgg  1260
aggaggcaca gatgtgtcta tggagggcat gaaaacccgaa gtggtggaga cgcttacccc  1320
tccaccctca gacgccggct caccctccca gagtagcccc ttgtcttttg gcagcagagc  1380
tagcagcagt ggtggtagtg actctgagcc cgacagtcca gcctttgagg atagccaggt  1440
caaagcccag cggctgcctt cacacagccg aggcatgctg gaccgctccc gcctggccct  1500
gtgtgtactg gcctttctgt gtctgacctg caatcctttg gcctcgcttt tcggctgggg  1560
cattctcact ccctctgatg ctacgggtac acaccgtagt tctgggcgca gcatgctgga  1620
ggcagagagc agagatggct ctaattggac ccagtggttg ctgccacccc tagtctggct  1680
ggccaatgga ctactagtgt tggcctgctt ggctcttctc tttgtctatg ggaacctgt    1740
gactaggcca cactctggcc cggctgtaca cttctggaga catcgcaaac aagctgacct  1800
ggatttggcc cggggagatt tcccccaggc tgctcaacag ctgtggctgg ccctgcaagc  1860
gctgggccgg ccccctgccca cctcaaacct ggatctggcc tgcagtctgc tttggaacct  1920
catccgccac ctgctccagc gtctctgggt gggccgctgg ctggcaggcc aggccggggg  1980
cctgctgagg gaccgtgggc tgaggaagga tgcccgtgcc agtgcccggg atgcggctgt  2040
tgtctaccat aagctgcacc agctgcatgc catgggcaag tacacaggag gacatcttgc  2100
tgcttctaac ctggcactaa gtgccctcaa cctggctgag tgcgcaggag atgctatctc  2160
catggcaaca ctggcagaga tctatgtggc agcggccctg agggtcaaaa ccagcctccc  2220
aagagccctg cacttcttga cacgtttctt cctgagcagc gccgccagg cctgcctagc    2280
acagagcggc tcggtgcctc ttgccatgca gtggctctgc caccctgtag gtcaccgttt  2340
ctttgtggac ggggactggg ccgtgcacgg tgcccccccg gagagcctgt acagcgtggc  2400
tgggaaccca gtggatccgc tggcccaggt gacccggcta ttccgtgaac atctcctaga  2460
gcgagcgttg aactgtattg ctcagcccag cccaggggca gctgacgag acagggagtt    2520
ctcagatgcc cttggatatc tgcagttgct aaatagctgt tctgatgctg ccggggctcc  2580
tgcttgcagt ttctctgtca gctccagcat ggctgccacc actggcccag cccagtggc    2640
caagtggtgg gcctcactga cagctgtggt gatccactgg ctgaggcggg atgaagaggc  2700
agctgagcgc ttgtacccac tggtagagca tatcccccag gtgctgcagg acactgagag  2760
accccctgccc agggcagctc tgtactcctt caaggctgcc cgggctctgc tggaccacag  2820
aaaggtggaa tctagcccag ccagcctggc catctgtgag aaggccagtg ggtacctgcg  2880
ggacagctta gcctctacac caactggcag ttccattgac aaggcatgc agctgctcct    2940
```

```
gtgtgatcta cttcttgtgg cccgtaccag tctgtggcag cggcagcagt caccagcttc    3000
agtccaggta gctcacggta ccagcaatgg accccaggcc tctgctctgg agctgcgtgg    3060
tttccaacat gacctgagca gcctgcggcg gttggcacag agcttccggc ctgctatgag    3120
gagggtattc ctacatgagg ccacagctcg gctgatggca ggagcaagtc ctgcccggac    3180
acaccagctc ctggatcgca gtctgaggag agggcaggt tccagtggca aggaggcac     3240 tacagctgag ctggagccac ggcccacatg gcgggagcac accgaggccc tgctgttggc    3300
atcctgctat ctgcccctg ccttcctgtc ggctcctggg cagcgaatga gcatgctggc     3360
cgaggcggca cgcaccgtag agaagcttgg cgatcaccgg ctactgctgg actgccagca    3420
gatgctcctg cgcctgggcg gcggaaccac cgtcacttcc agctagaccc caaagctttc    3480
ccttgaggac ctttgtcatt ggctgtggtc ttccagaggg tgagcctgac aagcaatcag    3540
gaccatgccg acctctagtg gcagatctgg aaattgcaga ggctgcactg gcccgatggc    3600
accctcttgc tctgtaggca ccttagtggc ttttccctag ctgaggctca ccctgggaga    3660
cctgtacata gtgtagatcc ggctgggcct ggctccaggg caggcccatg tactactttg    3720
acttttgcaa actttatttt cataggttga gaaattttgt acagaatatt aaaaaatgaa    3780
attatttata acttcagttt tgtttatctg ggtaggcaga tgtctgcctc agctgattgc    3840
tatctttcct ggcttgtcct ttgggaagcc ggacttccca tctgttgtaa ggtgtatttg    3900
ctggcttggt gatgctatgt tgagccacct tggccctctg atctcatggc tcataaccct    3960 tgagggcct tgatggtctc agttgttcct ttgccttcca gccctccacc aggtaataac     4020
cccgtatatc cagaaacaca cacagttccc tagtcatctc tgtgcaccag cataggcgaa    4080
ggatcagggc ccattagtga gtagactggg aaccctgttt tgtgccccg gccccttccc     4140 tctactccca acccttagg gaatctggtc ggcatccaca ggccgcacac ttccaaaaca     4200
atcgtggtat ctttattgac tttttttttt ctgaatgcaa tgactgtttt tttttttttt    4260
aactcttaag gaaaataaac atcttttaga aacagctcg                           4299
```

<210> SEQ ID NO 11
<211> LENGTH: 2245
<212> TYPE: DNA
<213> ORGANISM: Artificial sequence
<220> FEATURE:
<223> OTHER INFORMATION: GK

<400> SEQUENCE: 11

```
atgctggatg acagagccag gatggaggcc accaagaagg aaaaggtaga gcagatcctg      60
gcagagttcc agctgcagga ggaagacctg aagaaggtga tgagccggat gcagaaggag     120
atggaccgtg gcctgaagct ggagacccat caggaggcca gtgtaaagat gttgcccacc     180
tacgtgcgtt ccaccccaga aggctcagaa gttggagact ttctctcctt agacctggga     240
ggaaccaact tcagggtgat gctggtgaaa gtggggagg ggaggcagg acagtggagc       300 gtgaagacga aacaccagat gtattccatc cccgaggacg ccatgacggg cactgcggag    360
atgctctttg actacatctc tgagtgcatc tctgacttcc tggacaagca tcagatgaaa    420
cacaagaaac taccctgg cttcaccttc tccttccctg taaggcacga agacatagac     480
aagggcatcc tgctcaactg gaccaagggg ttcaaggcct ccggagcaga agggaacaac    540
atcgtgggac ttctccgaga tgctatcaag aggagagggg actttgagat ggatgtggtg    600
gcaatggtga atgacacggt ggccacaatg atctcctgct actatgaaga ccgccaatgt    660
gaggtcggca tgattgtggg caccggctgc aacgcctgct acatggagga gatgcagaat    720
```

-continued

```
gtggagctgg tggaaggcga tgaggggcgc atgtgtgtca acacagagtg gggcgccttc    780
gggaactccg gtgagctgga cgagttcctc ctggagtacg accggatggt ggatgagagc    840
tcagtgaacc ccggtcagca gctgtacgaa aagatcattg cggaaagta catgggcgag     900 ctggtacgac ttgtgctgct caagctggta gaggagaatc ttctgttcca cggagaggcc    960
tcagagcagc tgcgcacacg tggtgctttt gagacccgtt ttgtgtcgca ggtggagagc   1020
gactctgggg accgaaggca gatccttaac atcctgagca ctctgggcct tcgaccctct   1080
gtcgccgact gcgacattgt gcgccgtgcc tgtgaaagcg tgtccactcg cgccgcccac   1140
atgtgctcag caggactagc gggggtcata atcgcatgc gcgaaagccg cagtgaggac     1200
gtgatgcgca tcacggtggg cgtggatggc tccgtgtaca agctgcaccc gagcttcaag   1260
gagcggtttc acgccagtgt gcgcaggctg acacccaact gcgaaatcac cttcattgaa   1320
tcagaggagg gcagcggcag gggagccgca ctggtctctg cggtggcctg caagaaggct   1380
tgcatgctgg gccagtgaaa tccaggcaag gacagggacc tgggttccac ggggactcca   1440
caccccacaa atgctcccag tccactaggg caggagacct attctgctgc taccctgga    1500 aaatggggag aggcccctgc aagccaagtc agccagtgag acagccctag gctctcagc    1560 ctggggcaag gggcaagagg atcagcggca ccaaaagcct ttcttgctag aatcaactac   1620
agagaaaggt gaagcacact caggtcttgc tctttcagct tctggcctcc acagctgtg    1680 ggtctggcct cccaagggag tgcctcctgg acttgcaatg gcctggcttc cctgggaaca   1740
catctccatg gggaggtagc ttcagcagct tggccagacc agacctgggc ccccagaaga   1800
gtaagggctg cccagacctg gctgtttttct tgcctgtggc tgaagaggct gcaaaaccat   1860
gggagaccga ctatctagct acatggaggg gactttccag gccacaaaca ttccagagac   1920
agtctccttc atatacctcc accctgagt ggcttacagt tctgggatga accctcctag     1980
gagatgccag aggatagagg cccagagtcc ttgctctagg ggacctgaag gggagcgcct   2040
cactctgcac tgttagcagg atggcagctt caacactcac atcagtgatc cgggaagaga   2100
agcaagccac ccacagcatc tctccaggaa accacccagg tccctctgtc cctcatccct   2160
gtcaggtttc ccagatgcca tgccgccctc tccacaccag cttggaacca tgggggagtt   2220
tttaattaaa tatttaaaac tactt                                          2245
```

<210> SEQ ID NO 12
<211> LENGTH: 3587
<212> TYPE: DNA
<213> ORGANISM: Artificial sequence
<220> FEATURE:
<223> OTHER INFORMATION: NrF1

<400> SEQUENCE: 12

```
ctcggcggcg gcggcggcgg cagaggcggc agcgctcgcc attgccgctg gtggcaggag     60
gctgcgagga gccggcgcgg tcgcagtctc cacggcgcag gcccacggta gcgcagccgc    120
tctgaggtcg aatggtatgt ggttcatgta gaccacattt tgtttccctc tcacccattg    180
atggacactt gggtagcttc cattttggc tgttgtgaat aatgctgcta tgaacatggg    240
tgtgcacaga gctctctgag acgctgcttt cagtccttct ggcagtagat cttcatggag    300
gagcacggag tgacccaaac tgaacacatg gctaccatag aagcccatgc agtggcccag    360
caagtccagc aggtccatgt agccacgtac actgagcaca gtatgctaag tgctgatgaa    420
gactcccctt cctcccccga ggacacttct tatgatgact cggacatcct caactccacg    480
gcagctgatg aggtaactgc ccatctggct gctgcaggtc ctgtgggaat ggccgctgct    540
```

```
gctgctgtgg caacagggaa gaaacggaaa cggcctcatg tgtttgagtc taatccatct    600
atccgaaaga gacagcagac acgtttgctt cggaaactca gagccacgtt ggatgagtac    660
acgacgcgag tgggacagca agcgattgta ctctgcatct caccctccaa acccaaccct    720
gtcttcaagg tgtttggcgc agcacctttg gagaatgtgg tgcgaaagta caagagcatg    780
atcctggaag acctcgagtc tgctctggca gaacacgccc ctgcgccaca ggaggttaat    840
tcagagctgc cgcctctcac catcgatggg attccagtct ctgtggacaa aatgacccag    900
gctcagcttc gggcatttat cccagagatg ctcaagtatt ccacaggtcg ggggaaacca    960
ggctggggga agaaaagctg caagcctatc tggtggccag aagatatccc atgggccaat   1020
gtccgcagtg atgtccgcac agaagagcaa aaacaaaggg tttcatggac ccaggcatta   1080
cggaccatag ttaaaaattg ctataagcaa catgggcggg aggatctttt atatgctttt   1140
gaagatcagc aaacacaaac tcaggccacc accacacaca gtatagctca tctcgtacca   1200
tcacagaccg tagtacagac cttcagcaac cctgatggca ccgtgtcgct catccaggtt   1260
ggtacagggg caacagtagc cacattggct gatgcttcag aactgccaac cacagtcact   1320
gttgcccaag tgaattactc tgctgtggct gatggagagg tggaacaaaa ctgggccacg   1380
ttacagggcg gtgaaatgac catccagacg acgcaagcat cagaggccac ccaggcggta   1440
gcatcactgg cagaagccgc agtggcagct tctcaggaga tgcagcaggg agccactgtc   1500
accatggccc tcaacagtga agctgccgcc catgctgtcg ccactctggc ggaagccacc   1560
ttacaaggtg ggggacagat agtcctgtct ggggaaaccg cagcagccgt cggagcactt   1620
actggagtcc aagatgctaa tggcctggtc cagatccctg tgagcatgta ccagactgtg   1680
gtaaccagcc tcgcccaggg caacgggccg gtgcaggtgg ccatggcccc agtgaccacc   1740
aggatatcgg acagcgcagt caccatggat ggccaggctg tggaggtggt gaccttggaa   1800
cagtagcatg gagctctatc atggcagcgt ttttctagtct actgcagaat tttttacatg   1860
tttgcagagg tgcaatcaaa tggaattaag tctctcgact tggaaagaaa gttttggtaa   1920
ccttttttta agaaggaaga aaggcagcag attttggaat cacacttttt taaagcacca   1980
ctctgggatc tggtggaatg aacgccaccg atttcactgt cccaaaaagc caaattgtgg   2040
ccagacttct ttgtgcagaa atgtgtgtat acttacgtgt gtgtacgtgt gagtgtgaat   2100
atatgtatat gtgtacatat ggacatacac atttacatat atgtataaag tatatatgta   2160
catacataca tatgtatgaa acctgcatgg aattacctgt atgaaatcaa ggtgaactgt   2220
gggaacaaga accacccag attcgtgggt ggtagggtac atgaccaaac acagtcacct   2280
ggttttcgtt cataccaggg tcatgcattg agctactgac agactcaggc ggaggtgacc   2340
acgtccttca ccaaagctgc ctcccagtgg ccgcctagac ctctgctaga ttcaccgaag   2400
gaaggaagat ccaggacaca gcgtggtcca gagagtgctt gtgaagtcca gggacagaga   2460
gtgcgtgcgc acatgtgcgc tttgccagca gagacacacg gcagctggcc caggtgctga   2520
ccttgccaca ggcaggtaaa cgccctgcag gctcctggca ggggcaagaa atcgttcctc   2580
agcctccatc ttctccctte ccaggaaccc tcagtctcac gactattcaa gagttgcttg   2640
gttgtaaggt cagtcctgtt acaaactgaa ggtgacagaa gtgttaaggg tctgaggagt   2700
gttcatggag caggcgggtg taagtgcagg gtgtgtgtgt gtgtgtgtgt gtgtgtgtat   2760
gagtaatgga gaaaatggga agattatagg agagcaaaat aggaaggagg gagaaaactc   2820
ttcataaatc agggtgcgcc gtgggaaccg tgttctccag ctgtctgcag ctgtatttca   2880
gcagaggaga ctgcctcaca caggacctct gcgcaaaggc tggccgtcac agatgtgtca   2940
```

-continued

| | |
|---|---|
| gaagactctg tgaggacttt tcccaggcac atcctggcgg cacaggcctg ggacagcttt | 3000 |
| cctgctcaca gtgtggcttg cactgagcag tcattgtcac tgtgagcttc tgtgctttcc | 3060 |
| agccacaagc cctgagtctc ccgtggctca ttcatctgat gtcttgacaa gccaaatctc | 3120 |
| cactcctggc gtgcagggac tcttcctcct tcctgccagc cctctcccgt gcgtgatagt | 3180 |
| gtatttaatg tggtgttttt ggttttttgt ttttaatga cattaaaa gattcttcat | 3240 |
| gtcttgctca gcctttgaga aaagtttcca attcttatat ttgcttgttt tatataaaac | 3300 |
| tattcaatgt tctttgtatg ttcttttctg tatgtgataa gggaggggtg ggaaatttgc | 3360 |
| atatcaatgt cctggttcta caattggtta ctttttttt tttttaaac tgtgaagctg | 3420 |
| tccaggggct ttaaggcccg tgttcctttg tggtgaaata agcctcccga tagtttgaga | 3480 |
| aattgccaag aagataaaag caagatccca gcagcagagc atggaatctg tgttgttctc | 3540 |
| cattctgtct aaactgcctc attcaataaa tagtttaatg tggcgac | 3587 |

<210> SEQ ID NO 13
<211> LENGTH: 3918
<212> TYPE: DNA
<213> ORGANISM: Artificial sequence
<220> FEATURE:
<223> OTHER INFORMATION: tfam

<400> SEQUENCE: 13

| | |
|---|---|
| aacaagcccc cggagttccc acgctggtag tgtggcagtc cataggcacc gtattgcgtg | 60 |
| agacgaaccg gacggcgccg ggccatcatt cgtcggcccg agcgatggcg ctgttccggg | 120 |
| gaatgtggag cgtgctaaaa gcactggggc gcacggggt cgagatgtgc gcgggctgcg | 180 |
| ggggtcgcat cccctcgtct atcagtcttg tctgtattcc gaagtgtttt tccagcatgg | 240 |
| gtagctatcc aaagaaacct atgagttcat accttcgatt ttccacagaa cagctaccca | 300 |
| aatttaaagc taaacaccca gatgcaaaac tttcagaatt ggttaggaaa attgcagccc | 360 |
| tgtggaggga gctaccagaa gcagaaaaa aggtttatga agctgatttt aaagctgagt | 420 |
| ggaaagcata caagaagct gtgagcaagt ataaagagca gctaactcca agtcagctga | 480 |
| tgggtatgga aaggaggcc cggcagagac ggttaaaaaa gaaagcactg gtaaagagaa | 540 |
| gagaattaat tttgcttgga aaccaaaaa gacctcgttc agcatataac atttatgtat | 600 |
| ctgaaagctt ccaggaggca aaggatgatt cggctcaggg aaaattgaag cttgtaaatg | 660 |
| aggcttggaa aaatctgtct cctgaggaaa gcaggcata tattcagctt gctaaagatg | 720 |
| ataggattcg ttacgacaat gaaatgaagt cttgggaaga gcagatggct gaagttggac | 780 |
| gaagtgatct catccgtcga agtgtgaaac gatccggaga catctctgag cattaagatg | 840 |
| gaagacggag ttgtcattgg gattaggccc aagaaaccag ttaggtctca aagccttaaa | 900 |
| gtgtcaaact agaacggata aaggtggtta acctttgaca ttcagatcat ttttctgtag | 960 |
| ccatggactt tctgttaata ctttgagcct tgacagaaga tgatgctgag ttctgccttt | 1020 |
| tgcttaagaa ctggaacgga gactgtccat gcatctgcat gcagtggtga atcattctgc | 1080 |
| atttgatggg ctagatagac tgtgaagtga ctttcacact ggtgacagtt gtgtggtggt | 1140 |
| tttgtgatgt ttttacactg atgaccgtta catatgggtg tggcccttgg gtcccaggcc | 1200 |
| ggacctgctc tcccagctgt ggcagagctg tggataactg cattttcaaa gaagctgcca | 1260 |
| ggctttccta gatgaaatga ttcctagaca taaatcatgt gtaagttgat gtttgtatat | 1320 |
| aataagcgat tgctgatgtc ctgatagcat tttatagtag taacagagag atttacacat | 1380 |
| cttttctcaaa ttaagaaatt atgtaccaag tctatgcata ggttttctt gcatagaata | 1440 |

```
aaaactctaa ttttccaaac atgtttctga aattatgtat tttaagatga accatttggt      1500
taacagattt ttttttttc aattttaggt agggacttta gaaattactt ttcatttgag      1560
agtattcata gagcttgtgt ggtataaatt tttaaatgag aaaatgtgaa aaacaagtct      1620
gcaaagtcag aaatctgaaa gcttatccat gacagctaaa ggcctatgca ggagaaagcc      1680
aactgtggtg agccagccag gtccagctca ctaactgctc ttcagggcct actcatcaag      1740
aaatggattt atgttctaaa taggttttta aaaggaaag tatcagtgtg aaaattaata       1800
tgatctttag tgtttgtgaa tagaatttct tggaacacag ccacatgctt tcttgggttt      1860
gttgtgtgtg ggtgctctgt gctccagaga ctacactggg aaaccacagc atacagggat      1920
ggcccttcgc agacagtttg ccaccatggt gtctcacggc cactggccat gcaaggcttt      1980
tcctcagatg tccttgatgt ttctgtgata ttgtcaccct atcttggggt catcactggg      2040
tccctataag cctaactgtt ctctgtgtta gcaaggaaaa tattctttaa cctggaatcc      2100
tggtgtagca cagtacagaa gaccactgtg tggagcgaga ccctcctaat ctttactgtt      2160
gcacaggaaa aagtgtcttc cccactttga gctggcaaat cccataagcc cttagagaac      2220
tcatggcttc aaccaccaca ccactgagca gatctctgag acacaggaca acagagttca      2280
tactcatgta tgttttgtat tgaggaggct tagagattgt acattttggg aaagtaagtt      2340
tgcagtcact gaacttgaca aggtaggaac agaagaacgc atggaggaga gatgtaagag      2400
ttatatatgt aaaacagggt atttgagctg ggtagaaaac ttgcctagaa tgtacaaggc      2460
cttggatcca aatcccagaa ctgcaactct ccccagaaga gataatcaga attttagaga      2520
tgaatttaag aaaatataat ttttcccgtg gattggaatt ctgggttgtt ggatggcatg      2580
ggtttaagcc atagtttgaa ggtggtggaa ggaggccagt gtgaaccagt gcagtctgtc      2640
tttccaaagt gcaaatccag gagagacgtg agctctacac gcccctggtt tctgaaaagg      2700
aactaactcc aagctgtcct tagaatggag aaaatggtga ctcagagaat tgaccatgtg      2760
cttcagagca actcaggagc agcaggcact acagcgatac agggatgccc ggacctctaa      2820
gatgtaacta cttagctcct agcttttccag gcaccctgca gagtgttcaa ggactcggag      2880
ctcagtctgg gaagggaatg ggaaaggtag aggcctgggc ggaagccttc tcatggtact      2940
tggttcagtt tggttttcct tgtttgtaaa acaagcttac tgataacatt gtaatctgct      3000
ttccatgtcc tgttttctaa cgacagagtc tcttttaagc aaaagcagtt gccagaggat      3060
cggggaggtg ttgggaggag ctgaaggcat gcggtgaagc tgcacaagct gacaagggct      3120
cagtgctgtt tctacttatt gtcatgtaac tgcaattggg ctgccctgtt ttccagtatc      3180
cttaaaaaca acaaacccta gttggtctaa gtgtgaacct ctgaatttaa agctggtgtt      3240
agcatacgga tgtacagtag ctagaaagcc ttcctgggtt cacccgcacg cactggacca      3300
ccagggggcg ctgaaaccac agctttaatg cagacggagc catagtgccc atcagttctg      3360
tttggccata ttataagaat tttcttcctc tgatagcaac cctcctttct cccaggtttt      3420
gtttatttgt ttttgtttgt tgtttgttt gtttgtttgt tttcgagac agggtttctc       3480
tgcgttgccc tgcctgtcct gtaactcact ttgtagacca gctggctgta gactcggaga      3540
cctacctcag attaagtgct gagattaaga gcttgcctca ccaccaccat caggcttcct      3600
ccctcctctt ccgaatttgc caccagcctg tcactgacaa gtttgcaaat gctaaaacag      3660
tgcctgtatg ttttgaagtg taaagaacat atttctttt ttgtaattga gcttaagaga       3720
taaaatgaat gtattactca tttgtaaaac ttcctaagca aaaggtaaaa ttatgcacaa      3780
ctggtaacca tcaattgttt atcattcaca aatcaaatat tttcgttatt taaccactga      3840
```

-continued

```
tagtaattca ttataaaacc attcttttgc acagttagga atgctgacca agaaactgca    3900
ttatttaaat taaatgct                                                  3918
```